(12) United States Patent
Thomas

(10) Patent No.: US 10,687,992 B2
(45) Date of Patent: Jun. 23, 2020

(54) FORMED FILM ACQUISITION DISTRIBUTION LAYER AND ABSORPTIVE DEVICE THEREWITH

(71) Applicant: Tredegar Film Products LLC, N. Chesterfield, VA (US)

(72) Inventor: Paul Eugene Thomas, Terre Haute, IN (US)

(73) Assignee: TREDEGAR FILM PRODUCTS LLC, N. Chesterfiel, VA (US)

(*) Notice: Subject to any disclaimer, the term of this patent is extended or adjusted under 35 U.S.C. 154(b) by 450 days.

(21) Appl. No.: 15/299,067

(22) Filed: Oct. 20, 2016

(65) Prior Publication Data

US 2017/0105887 A1    Apr. 20, 2017

Related U.S. Application Data

(60) Provisional application No. 62/243,964, filed on Oct. 20, 2015.

(51) Int. Cl.
| | |
|---|---|
| *A61F 13/15* | (2006.01) |
| *A61F 13/513* | (2006.01) |
| *A61F 13/537* | (2006.01) |
| *B29C 59/06* | (2006.01) |

(Continued)

(52) U.S. Cl.
CPC ...... *A61F 13/513* (2013.01); *A61F 13/15731* (2013.01); *A61F 13/537* (2013.01); *A61F 2013/15926* (2013.01); *A61F 2013/51078* (2013.01); *A61F 2013/51147* (2013.01); *A61F 2013/51165* (2013.01);

(Continued)

(58) Field of Classification Search
CPC .............. A61F 13/513; A61F 13/537; A61F 2013/51078; A61F 2013/51338; A61F 2013/51355; A61F 2013/53721; A61F 2013/53782

See application file for complete search history.

(56) References Cited

U.S. PATENT DOCUMENTS

| | | | |
|---|---|---|---|
| 3,929,135 A | 12/1975 | Thompson | |
| 4,324,246 A * | 4/1982 | Mullane | A61F 13/512 604/366 |

(Continued)

FOREIGN PATENT DOCUMENTS

| | | |
|---|---|---|
| CN | 1446527 A | 10/2003 |
| CN | 1471380 A | 5/2005 |

(Continued)

OTHER PUBLICATIONS

International Search Report and Written Opinion dated Jan. 12, 2017, for International Patent Application No. PCT/US2016/057930.

(Continued)

*Primary Examiner* — Jacqueline F Stephens
(74) *Attorney, Agent, or Firm* — Karceski IP Law, PLLC

(57) ABSTRACT

An absorptive device includes a topsheet, a backsheet, an absorbent core between the topsheet and the backsheet, and an acquisition distribution layer between the topsheet and the absorbent core. The acquisition distribution layer includes a formed film having a plurality of lands that contact a bottom surface of the topsheet and define an irregular array of cells.

18 Claims, 22 Drawing Sheets

(51) Int. Cl.
*A61F 13/511* (2006.01)
*A61F 13/51* (2006.01)

(52) U.S. Cl.
CPC .............. *A61F 2013/51338* (2013.01); *A61F 2013/51355* (2013.01); *B29C 59/06* (2013.01)

(56) References Cited

U.S. PATENT DOCUMENTS

| | | | |
|---|---|---|---|
| 4,342,314 A * | 8/1982 | Radel | A61F 13/15731 428/116 |
| 4,509,908 A | 4/1985 | Mullane, Jr. | |
| 4,601,868 A | 7/1986 | Radel et al. | |
| 4,964,860 A * | 10/1990 | Gipson | A61F 5/4401 604/391 |
| 6,610,904 B1 | 8/2003 | Thomas et al. | |
| 8,460,778 B2 | 6/2013 | Thomas et al. | |
| 2004/0002688 A1* | 1/2004 | Thomas | A61F 13/53717 604/383 |
| 2013/0304012 A1 | 11/2013 | Zhao et al. | |
| 2014/0303585 A1 | 10/2014 | Seyler | |

FOREIGN PATENT DOCUMENTS

| | | |
|---|---|---|
| CN | 101268126 A | 9/2008 |
| CN | 201445606 U | 5/2010 |
| CN | 203724323 U | 7/2014 |
| CN | 204655297 U | 9/2015 |
| WO | WO 0224133 A1 | 3/2002 |
| WO | 2016064861 A1 | 4/2016 |

OTHER PUBLICATIONS

International Preliminary Report on Patentability dated Apr. 24, 2018, for International Patent Application No. PCT/US2016/057930.
Supplementary European Search Report dated May 7, 2019, for European Patent Application No. 16858221.
Chinese Office action dated Sep. 3, 2019, for Chinese Office Action No. 201680061461.7.
European Office Action dated Jan. 2, 2020, for European Patent Application No. 16858221.1.
Chinese Office Action dated Apr. 2, 2020, for Chinese Patent Application No. 201680061461.7.

* cited by examiner

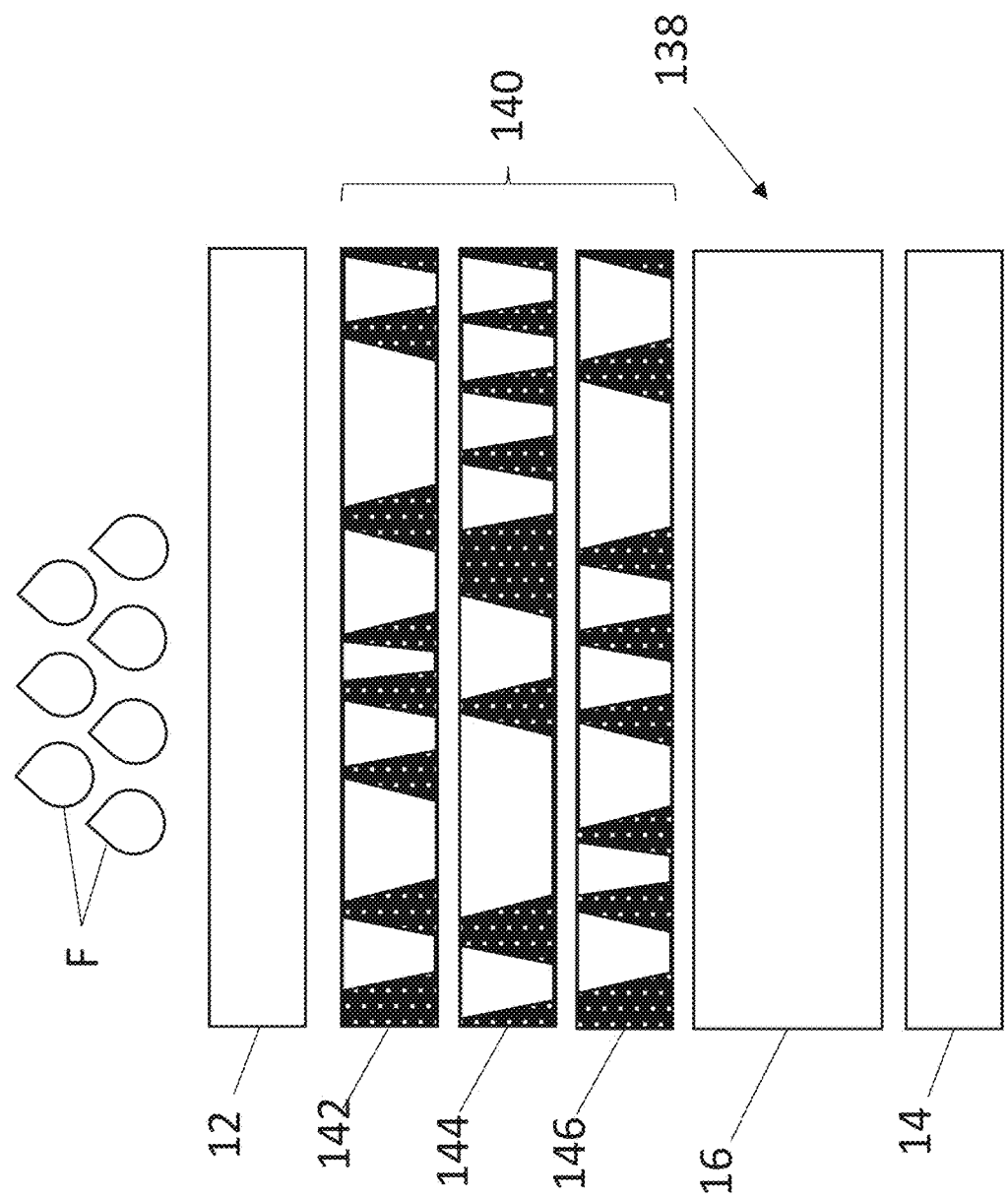

FORMED FILM ACQUISITION DISTRIBUTION LAYER AND ABSORPTIVE DEVICE THEREWITH

CROSS-REFERENCE TO RELATED APPLICATIONS

This application claims the benefit of priority from U.S. Provisional Patent Application Ser. No. 62/243,964, filed Oct. 20, 2015, the content of which is incorporated herein by reference in its entirety.

FIELD

The present invention is related to a formed film acquisition distribution layer for an absorptive device, such as an adult incontinence product or baby diaper. The present invention also relates to an absorptive device with a formed film acquisition distribution layer therein.

BACKGROUND

Topsheets comprised of formed films were designed to be useful in absorptive devices for reducing "rewet." Rewet may be the tendency for fluids absorbed in the absorbent core to come back onto the skin. Using a formed film topsheet creates a drier surface to the user after fluid insults and have been primarily functional in the feminine napkin use. However, the vast majority of women, about 60% or more, prefer the comfort of a nonwoven topsheet.

While nonwoven topsheets may be more comfortable, especially being worn in non-menstrual days in anticipation of needing protection soon, nonwoven topsheets will wick fluids back to the skin during menstrual days causing rewet, whereas a formed film topsheet generally will not cause rewet. A typical formed film topsheet may occlude the skin with a skin contact area of at least about 27.5%, with some films as high as 62.5%, which may cause a clammy feeling when worn on pre-menstrual days, because the skin occlusion area may not allow the skin's sweat to evaporate to the open atmosphere. The skin may not be able to "breathe" when occluded by a plastic, fluid impermeable region. The skin contact area essentially correlates to what may be called the "land surface area" of a formed film.

It was later discovered that by placing a formed film topsheet in a sublayer position beneath a nonwoven topsheet, the wearer benefited by having some of the comfort of the nonwoven, plus the reduction of rewet. The skin occlusion factor of the formed film was not completely eliminated because the combination also created a zone of residual wetness at the interface between the film's land surface area and the nonwoven laying upon it. Although not ideal, the formed film sublayer, which was used for reducing rewet by having no wicking, created a dryer surface in use, even with the residual wetness that was introduced, as compared to nonwoven topsheet alone or nonwoven topsheet and nonwoven sublayers between the topsheet and the core.

In addition, formed film topsheets used as sublayers served to reduce rewet, but did not distribute the fluids after the insult region had become saturated by multiple insults. This may have been especially recognized in diapers. After at least about 2 to 3 insults (depending on the core's construction and components) the core region in proximity with the insult position becomes saturated. The structure of the formed film topsheets did not provide sufficient void space to let the unabsorbed fluids of the $4^{th}$ or $5^{th}$ insults move laterally to be distributed to unused regions of the core.

In order to address this issue, additional formed films known as "acquisition distribution layers" (also known as "ADLs") emerged useful as sublayers that reduce rewet, but could also distribute fluids to unsaturated regions of the core. ADLs were developed to provide the fluid distribution performance that was lacking by merely laying a formed film topsheet in a sublayer position between a nonwoven topsheet and an absorbent core. Acquisition distribution layers typically have a high void volume and may be designed for rapid acquisition of insult fluids and broader distribution of the fluids to other areas in the absorbent core once the area of the core that is in the insult region has become saturated by previous insults. When the absorbent core area that is in the insult region becomes saturated by multiple insults, volume space is sufficient to allow the fluids to move laterally to unused regions of the core. To date, however, these films remained comprised of, although in a larger scale, a uniform repetitive array of geometrically shaped formed film cells.

A formed film acquisition distribution layer with high void space that may be useful for distribution of insult fluids, but have the repetitive array of geometrically shaped cell depressions, may also have an excessive land surface area that holds residual wetness and occludes the skin as it lies beneath a nonwoven topsheet. A new problem has also been observed with the acquisition distribution layers of the prior art in that the regularly shaped and spaced apart repetitive arrays of cell depressions can cause "skin marking" on a baby's buttocks with overnight use where the baby is lying prone on the diaper. This skin marking, the pressing and temporary maintaining of the pattern in the baby's skin (something like a pillow wrinkle on one's face in the morning), may cause the baby's parent to think the baby has obtained a rash.

In addition, the repetitive array of wells, holes, cells, depressions, or other synonymous terms, can be visible to the parent beneath the nonwoven topsheet. Unfortunately, this negative visual "trigger" of seeing this repetitive array of similar geometric shaped cells may cause some parents to avoid buying the product, even though it is very functional and provides for a healthier skin for their baby. As such, current acquisition distribution layers may not maintain the functions of rapid acquisition and distribution of insult fluids, may not be invisible to the parent, and also may not provide for less residual wetness and skin occlusion land surface area.

These deficiencies in the prior art have lead those skilled in the art to seek further improvements to acquisition distribution layers and absorptive devices incorporating such acquisition distribution layers.

SUMMARY

It is desirable to improve the functionality of acquisition distribution layers for use in absorptive devices, such as adult incontinence products or baby diapers. Described herein is an acquisition distribution layer that may be used (e.g., primarily but not exclusively) in, for example, a diaper, such as a baby diaper, with a high void volume space for enhanced fluid distribution while maintaining high acquisition rate and having the features of being "invisible" to the parent, while also having a very low skin occlusion/residual wetness land surface area. In an embodiment, the acquisition distribution layer may include at least a top tier that may be a leather grain artwork having an irregular array of lands that may both camouflage with the randomized distribution of the fibers of a nonwoven topsheet and may have a low skin contact/surface wetness land surface area.

According to an aspect of the invention, there is provided an absorptive device that includes a topsheet, a backsheet, an absorbent core between the topsheet and the backsheet, and an acquisition distribution layer between the topsheet and the absorbent core. The acquisition distribution layer includes a formed film having a plurality of lands that contact a bottom surface of the topsheet and define an irregular array of cells.

According to another aspect of the invention, the irregular array of cells has a random variety of shapes forming no regular geometric shapes.

It is contemplated that the irregular array of cells may be configured to render the plurality of lands invisible to a naked eye when the absorptive device is viewed from above the topsheet.

It is also contemplated that the topsheet may be a nonwoven topsheet.

In a further embodiment, the plurality of lands may be invisible by being camouflaged with the nonwoven topsheet.

In an alternative construction, the acquisition distribution layer may have a loft of at least about 775 microns. In other embodiments, the acquisition distribution layer may have a loft of about 1400 microns.

It is contemplated that at least some of the plurality of cells may have an inscribed circle diameter of between about 800 microns and about 1400 microns.

In one or more embodiments, top surfaces of the plurality of lands are contemplated to lie generally in a plane and to have a combined surface area that provides low skin occlusion and low residual wetness. To this end, it may be that the combined surface area is less than about 25% of an overall area of the acquisition distribution layer.

In another contemplated embodiment of the invention, the acquisition distribution layer may have multiple tiers. If so, top surfaces of the plurality of lands may define an upper tier.

In another aspect of the invention, at least one lower tier relative to the upper tier may be comprised of a second irregular array of cells.

Still further, it is possible that a lower tier relative to the upper tier has of a regular pattern of geometrically shaped cells having a repetitive pattern.

Where the absorptive device includes multiple tiers, the multiple tiers may include an upper tier having a loft of about 950 microns, a middle tier having a loft of about 690 microns, and a lower tier having a loft of about 220 microns.

The present invention also provides for an acquisition distribution layer that includes a plurality of lands and a plurality of cells surrounded by the plurality of lands. The plurality of lands are contemplated to define an array of the plurality of cells. Each of the plurality of cells in the array of the plurality of cells are contemplated to be irregularly shaped.

Consistent with other embodiments, the acquisition distribution layer is thought to have a construction where at least some of the plurality of cells have an inscribed circle diameter of between about 800 microns and about 1400 microns.

It is also contemplated that the plurality of lands may have a loft of about 1400 microns.

In one contemplated embodiment, the acquisition distribution layer may include a first tier defining a first plurality of lands, a first plurality of cells surrounded by the first plurality of lands in the first tier, a second tier defining a second plurality of lands, and a second plurality of cells surrounded by the second plurality of lands in the second tier. The first plurality of lands may define a first array of the first plurality of cells. The second plurality of lands may define a second array of the second plurality of cells. Each of the first plurality of cells in the first array may be irregularly shaped. Finally, each of the second plurality of cells in the second array may be irregularly shaped.

It is contemplated that at least some of the first plurality of cells and some of the second plurality of cells have an inscribed circle diameter of between about 800 microns and about 1400 microns.

Still further, the first plurality of lands and the second plurality of lands may have a loft of about 1400 microns.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIG. 22 is a graphical, exploded side view of an additional contemplated embodiment of an absorptive device according to the present invention.

DETAILED DESCRIPTION

Figure 1:
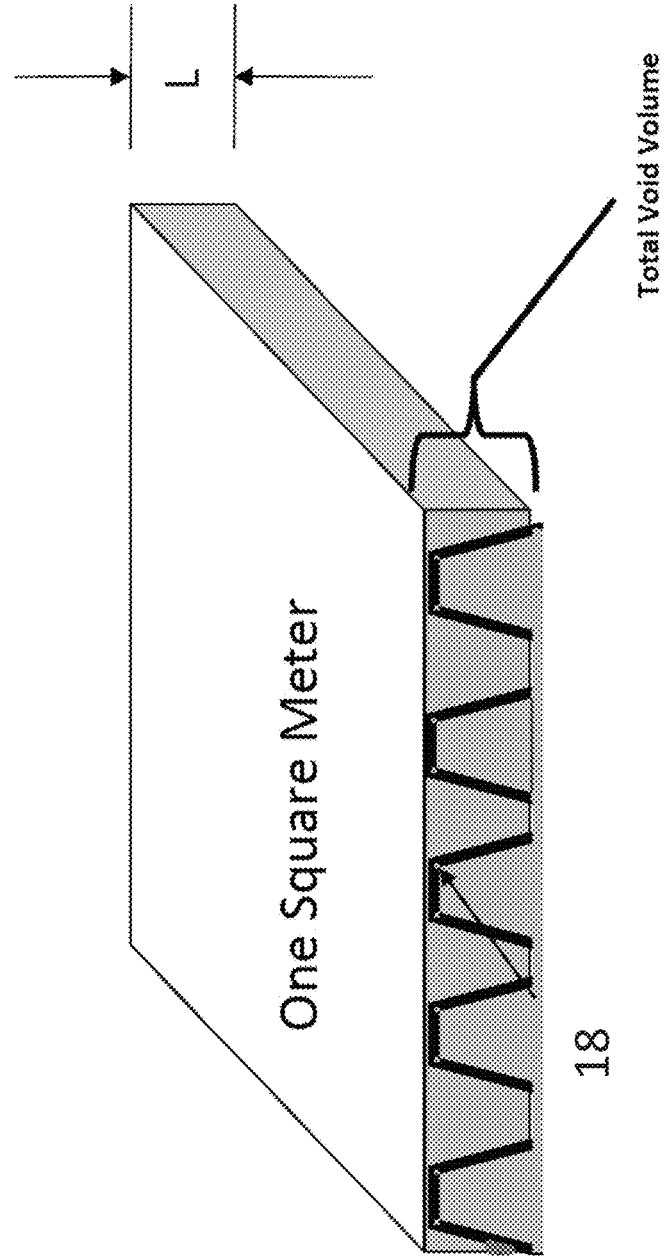
FIG. 1 is a perspective, graphical illustration assisting with a definition of the total void volume delineated by an acquisition distribution layer according to the present invention.

In examples and embodiments described herein, one or more of the following terms may be defined and/or used. Where employed, these terms are not intended to be limiting of the present invention. Instead, these terms are employed to assist with a discussion of the breadth and scope of the present invention, as should become apparent to those skilled in the art.

"Acquisition" is a term that refers to, but is not limited to, the ability for insult fluids, especially urine for a diaper application, to rapidly move into and through the acquisition distribution layer to then be absorbed in the absorbent core.

"Distribution" is a term that refers to, but is not limited to, the ability to allow fluids that have been acquired by the acquisition distribution layer, but cannot enter the saturated insult region of the core, to move laterally to new, unused areas of the core.

"Skin Occlusion" is a term that refers to, but is not limited to, an area of skin where the substantially impermeable plastic of the land surface area of the formed film blocks the skin, either by direct contact (such as in prior art formed film topsheets) or by near proximity to the skin with only a nonwoven topsheet between the skin and land surface area (such as prior art sublayers of topsheets or prior art acquisition distribution layers). As the acquisition distribution layer may be lying beneath a nonwoven topsheet, it is possible that some of the skin's pores cannot "breathe." In other words, the skin's release of sweat through its pores cannot evaporate to the open atmosphere because of the close proximity of the acquisition distribution layer to the user's skin, which may result in an uncomfortable, hot and clammy skin condition.

"Residual Wetness" is a term that refers to, but is not limited to, wetness that may become trapped at the interface between the formed film land surface area and the nonwoven topsheet. In connection with this phenomenon, it is noted the term "rewet" is often employed as a measurement for the potential for skin wetness during use of a formed film material in an absorptive device. The term "rewet" implies that the fluid fully entered the absorbent core and then returned to the skin or was reintroduced to the skin. The term "residual wetness," therefore, encompasses the wetness that did not pass through to the core but, instead, remains as moisture residue within the topsheet at the corresponding interfacial contact between the land surface area and the nonwoven material.

"Invisible" is a term that refers to, but is not limited to, the parent's inability to see through the nonwoven and recognize a repetitive array of depressions. As such, this term encompasses a property of a material that causes the material to be "hidden" from a user's visual perception. A material that is "invisible" also encompasses a material where the user, such as a parent, cannot see a repetitive array of skin markings on their baby's skin after all night use or similar situations.

"Camouflaged" is a term that refers to, but is not limited to, a way of hiding something by making it look like its background. In the context of the present invention, this term encompasses methods and devices that help make the background (i.e, the acquisition distribution layer) look like its foreground (the random laid fibers of a nonwoven).

"Tier" is a term that refers to, but is not limited to, a thickness and/or height of a layer of material, such as the acquisition distribution layer. In the context of the present invention, the term "tier" is contemplated to encompass Z direction for a formed film with a single vertical zone of an array of cells, each cell having a top and bottom comprised of a single general description of its land perimeter configuration. In this context, the Z direction includes the array of cells that are all within one tier, where any individual cell within a tier begins on the top plane and ends at the bottom plane of that tier. In multi-tiered embodiments, the bottom plane of an upper tier will generally coincide with the top plane of the next lower tier, but the present invention should not be understood to be limited solely to such a construction.

"Loft" is a term that refers to, but is not limited to, the total magnitude of the Z direction as measured value from the top most plane of the acquisition distribution layer to its lower most plane. For a film having a single tier, loft is synonymous with tier.

"Geometrically shaped cells" is a term that encompasses typical cell shapes of prior art formed films useful in absorptive devices. For example, European Patent No. EP 1 318 781 B2 (the contents of which are incorporated herein by reference) describes cells that have a hexagonal, circular, oval, elliptical, or polygonal shape. A "geometric polygon" has straight line on its perimeter, and ovals, ellipses, and circles have symmetrical patterns with arcuate perimeters.

"Repetitive pattern" is a term also employed in relation to formed films found in the prior art. U.S. Pat. No. 3,929,135 to Thompson (the contents of which are incorporated herein by reference) describes a formed film with a repetitive pattern. This patent describes generally tapered structures, including structures having a triangular, square, or polygonal base and a frustum of a pyramid. When the edges of such polygons are nested side-by-side, they are aligned so that each land has a substantially uniform and equal land width or a "repetitive pattern" of individual cells. In the case of ovals, circles, etc., it may be typical to have a pattern where their centers form a triangular or square. U.S. Pat. No. 4,509,908 to Mulane (the contents of which are incorporated herein by reference) shows examples of repetitive patterns from geometrically shaped cells, e.g., hexagons and circles.

"Leather grain artwork" and "leather grain" are terms that refer to, but are not limited to, forming screen artwork and/or patterns that produce a resulting formed film with the look of leather grain. In the context of the formed film according to the present invention, the leather grain encompasses the simulation of the irregular array of the leather grain's lines that are depressed into the surface of the leather. In the context of the formed film acquisition distribution layer according to the present invention, "leather grain" refers to the irregular array of the land perimeters around the formed film cells. Some leather grain artworks may be more suited to this art than others and some artworks can be slightly manipulated to enlarge the smaller cells, if needed, for improved and more balanced vacuum forming, as described herein.

"Irregular array" is a term that encompasses, but is not limited to, a construction where no individual formed film cell has a land perimeter which essentially forms any true polygon or other geometrically shaped cells. The nesting of these cells may present a side by side nesting in order to have an essentially uniform and narrow land width for enhancing low skin occlusion and reduced residual wetness that results from the land surface area. The resulting array may have no discernable repetitive pattern of cell geometries.

"Land surface area" is a term that refers to, but is not limited to, the total area of the lands in the top plane of the uppermost tier of the formed film acquisition distribution layer. It is contemplated that the land surface area of a particular formed film may be determined by applying black ink onto those lands and determining their percentage of area by comparison with the total area of the film. While not limiting of the present invention, this comparison may be performed using an image in an ImagePro unit.

"Total void volume" is a term that refers to, but is not limited to, the open volumetric space established by an acquisition distribution layer through which fluid travels. In the context of one prior art example, European Patent No. EP 1 318 781 B2 (the contents of which are incorporated herein by reference) describes a void space sufficient for lateral movement of fluids. The total void volume is calculated to be at least about 750 cc/square meter.

Referring to FIG. 1, if a sheet of acquisition distribution layer is cut into one square meter and has its loft L measured, the loft may be substantially equivalent to the Total Void Volume as calculated below:

1 micron=0.0001 cm
$m^2$=100 cm×100 cm=10,000 $cm^2$
Loft in microns×0.0001=Loft in cm
ACQUISITION DISTRIBUTION LAYER Film's Loft is at least=775 microns
775×0.0001=0.0775 cm
0.0775 cm×10,000 $cm^2$=775 $cc/m^2$
Remove Estimated Film Mass of 3%
775×0.97=Total Void Volume @ 750 $cm^3/m^2$ As such, if one maintains a loft of at least about 775 microns, there may be sufficient void volume for lateral flow. This may be a feature or element of examples herein needed to maintain good acquisition distribution layer performance. Unfortunately, in the European Patent referenced above, the geometrical shape of cells in a repetitive pattern present inherent problems, as discussed above.

Figure 2:
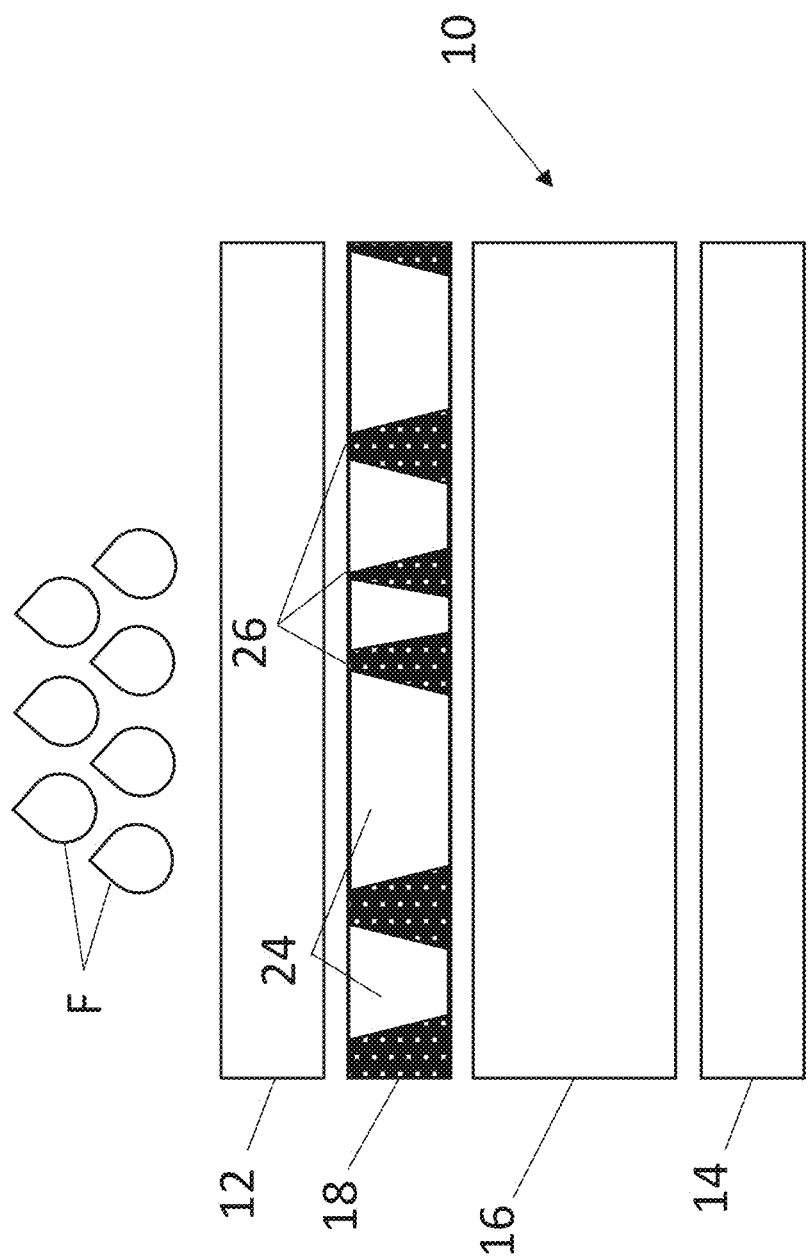
FIG. 2 is a graphical, exploded side view of one contemplated embodiment of an absorptive device according to the present invention.

FIG. 2 schematically illustrates an absorptive device 10 in accordance with embodiments of the invention. The absorptive device 10 may be a baby diaper, an adult incontinence product, a feminine hygiene product, such as a sanitary napkin, or any other absorptive device in which fluids are moved away from a source of the fluid. As illustrated, the absorptive device 10 includes a topsheet 12, a backsheet 14, an absorbent core 16 between the top sheet 12 and the backsheet 14, and an acquisition distribution layer 18 between the top sheet 12 and the absorbent core 16. A source of fluid F located above the topsheet 12 of the absorptive device 10 deposits fluid F onto the topsheet 12, which passes the fluid F to the absorbent core 16 via the acquisition distribution layer 18. The absorbent core 16 stores the fluid F and the backsheet 14 prevents the fluid F from leaking out of the absorptive device 10. The topsheet 12 may be a formed film having apertures, a nonwoven material, and/or laminates thereof. The absorbent core 16 may include any suitable material that absorbs and holds fluids F, as known in the art. The backsheet 14 may be a plastic film that is configured to allow vapors, but not fluids F, to pass therethrough. Embodiments of the acquisition distribution layer 18 are described in further detail below.

Figure 3:
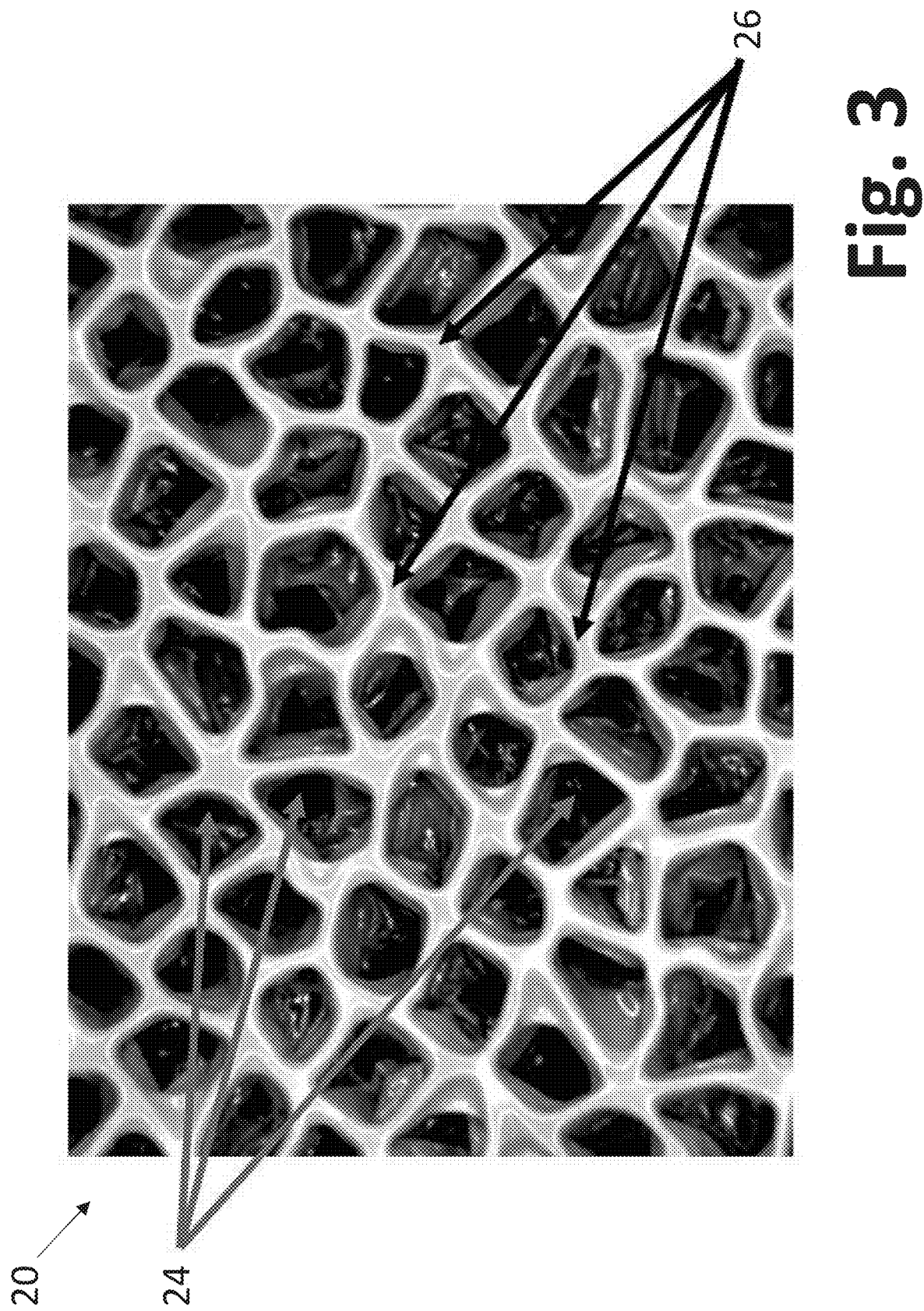
FIG. 3 illustrates a single tier leather grain artwork vacuum formed film made using the forming screen illustrated in FIG. 4.
Figure 4:
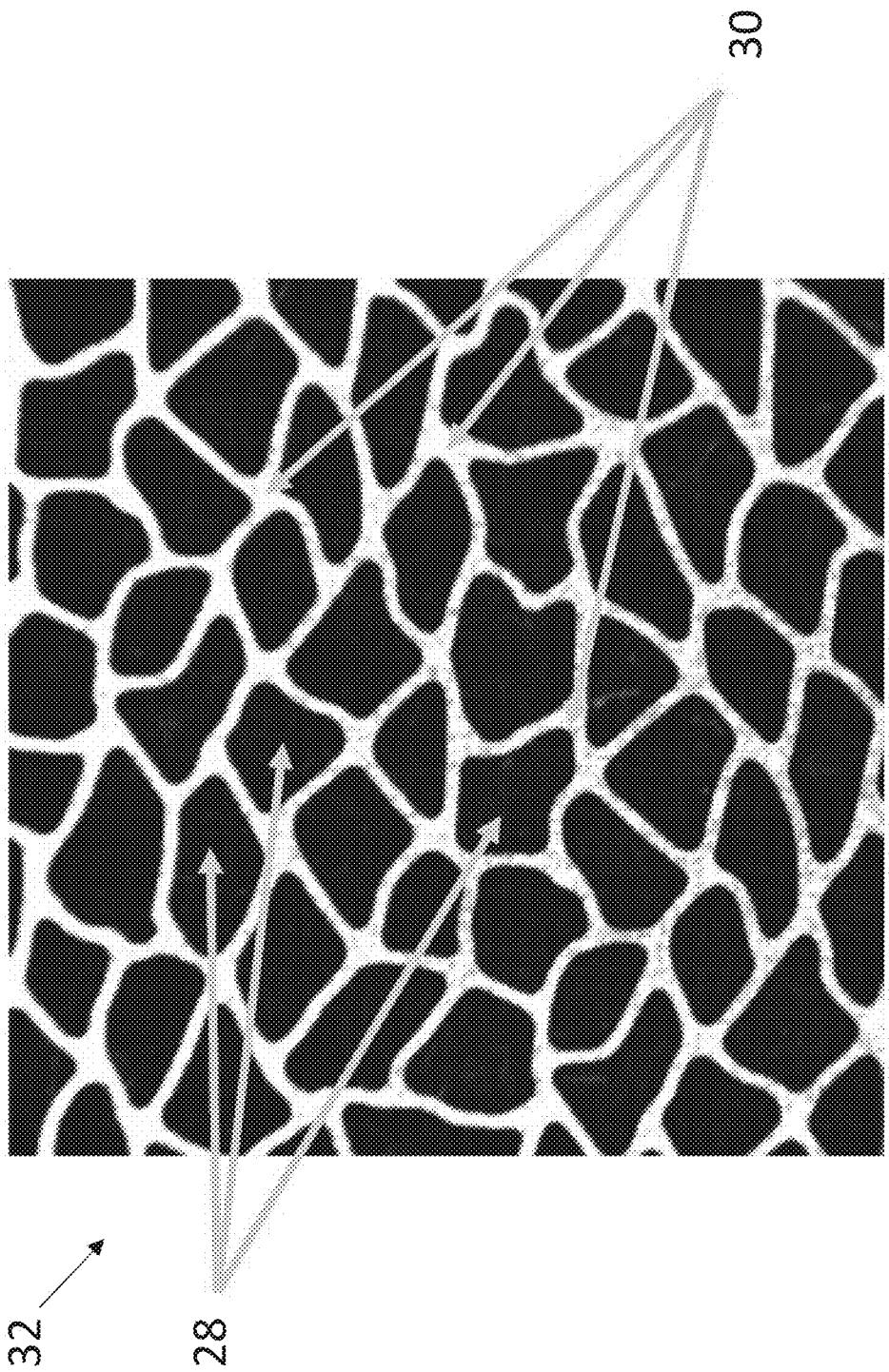
FIG. 4 is a graphical illustration of a forming screen that defines an array of cells for an acquired distribution layer according to the present invention.

FIG. 3 shows a single tier leather grain artwork vacuum formed film 20 made from a forming screen 32 illustrated in FIG. 4. The formed film 20 shown in FIG. 3 may include apertured cells 24 and land perimeters 26 surrounding the cells 24 which correspond to, and may have been formed by the corresponding cells 28 and lands 30 of the forming screen 32 of FIG. 4 by an applied pressure differential—in this case vacuum. High pressure water nozzles, high pressure air plenums and the like might also be used in some embodiments for applying sufficient pressure differential to form the array of cells 28 (also referred to as a cell array) of the forming screen 32 into a replicated array of cells 24 (also referred to as a cell array) of the formed film 20.

Figure 5:
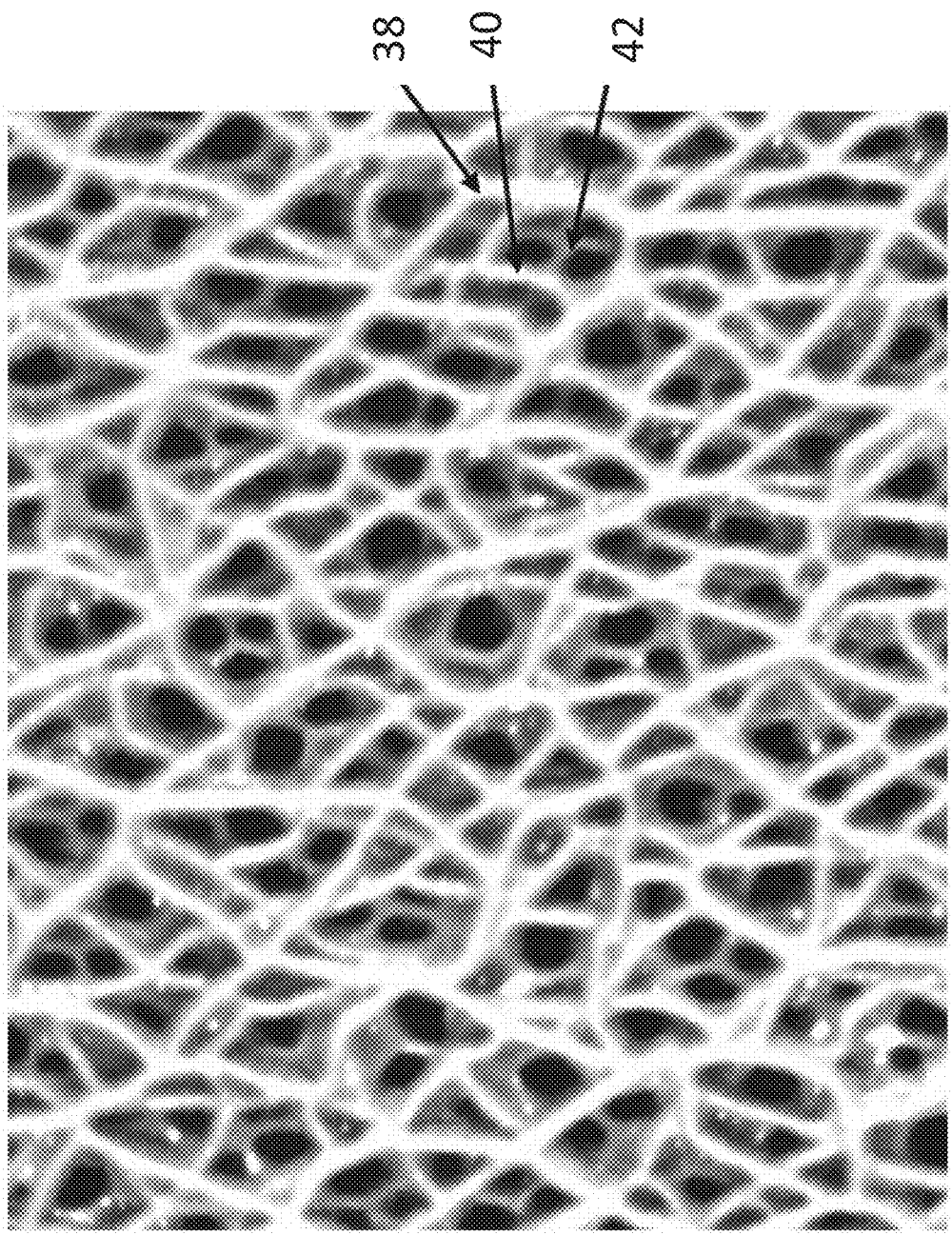
FIG. 5 illustrates one embodiment of a segment of a film formed from the forming screens illustrated in FIG. 6.
Figure 6:
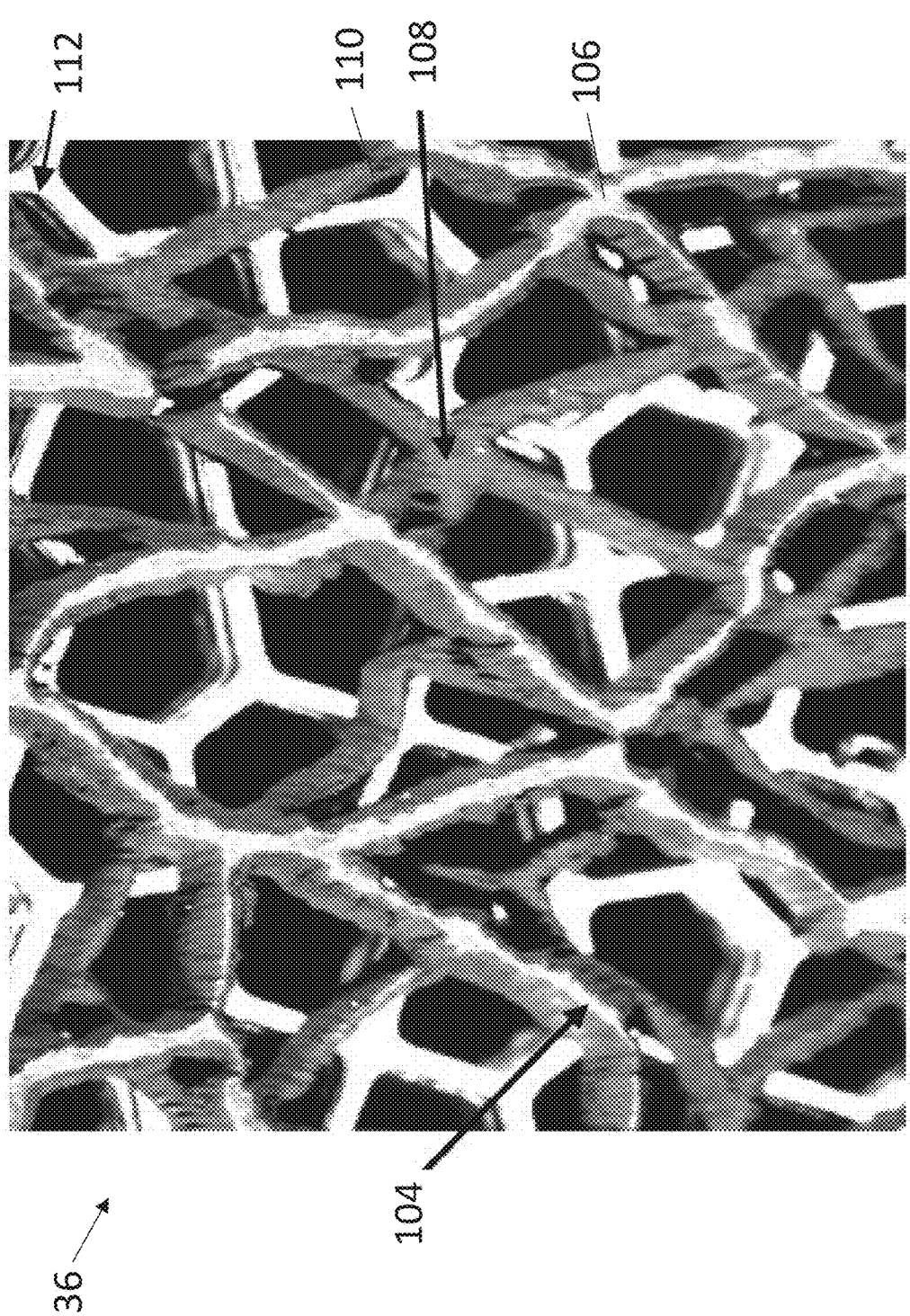
FIG. 6 illustrates another embodiment of a forming screen according to the present invention, where the forming screen includes two tiers of lands, and a base screen.

FIG. 5 shows a segment of a film 34 formed on the forming screen 36 of FIG. 6 having upper tier lands 38 surrounding and/or intersecting mid-tier lands 40, both formed in the thermoset engraved rubber portion of the screen 36 of FIG. 6. Mid-tier lands 40 may surround and/or intersect with lowest tier lands 42 that formed onto the exposed portions of a pentagon pattern of a base metal screen, as described in further detail below.

Figure 7:
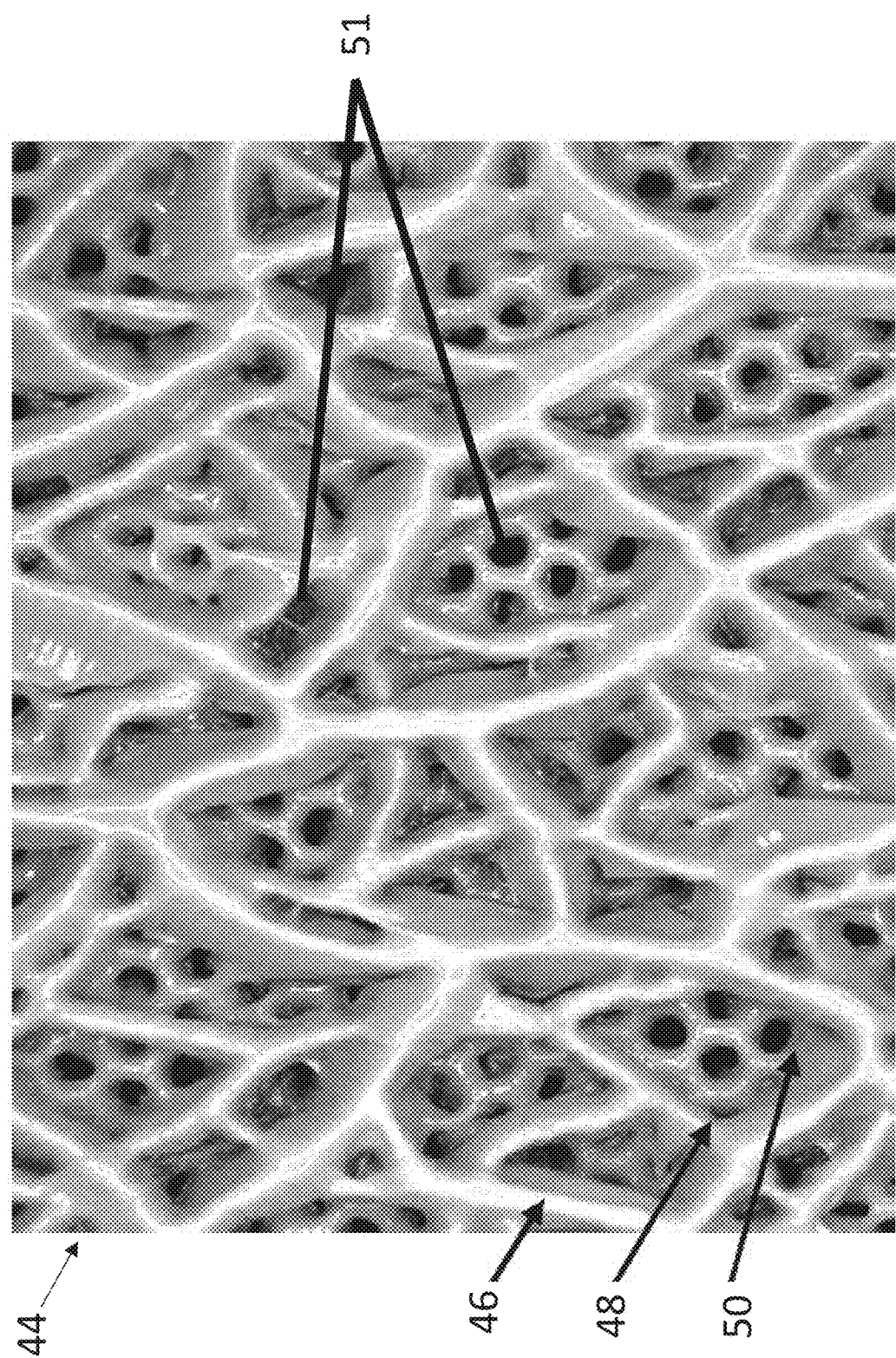
FIG. 7 illustrates another embodiment of a segment of a film formed from a forming screen shown in FIG. 6 and a base metal screen with a repetitive pattern of hexagonal cells.

In FIG. 7, a segment of a formed film 44 is shown that was formed from a screen where the top two tiers may again be those of the screen 36 of FIG. 6. In this embodiment, the base metal screen may have a repetitive pattern of cells of the geometric shape of a hexagon with mesh count of 40 mesh. The film 44 has an upper tier leather grain artwork of lands 46 surrounding and/or intersecting mid-tier leather grain artwork lands 48 which may be surrounding and/or intersecting lowest tier (40 mesh) lands 50. This film 44 may be useful if there may be a desire to slow down the acquisition rate of fluid F flowing directly into the cells 51 such that it momentarily dams up and is forced to "spill over" to next adjacent cells 51. The spill over function may be consistent with the description provided in U.S. Pat. No. 6,610,904, the content of which is incorporated herein by reference in its entirety.

Figure 8:
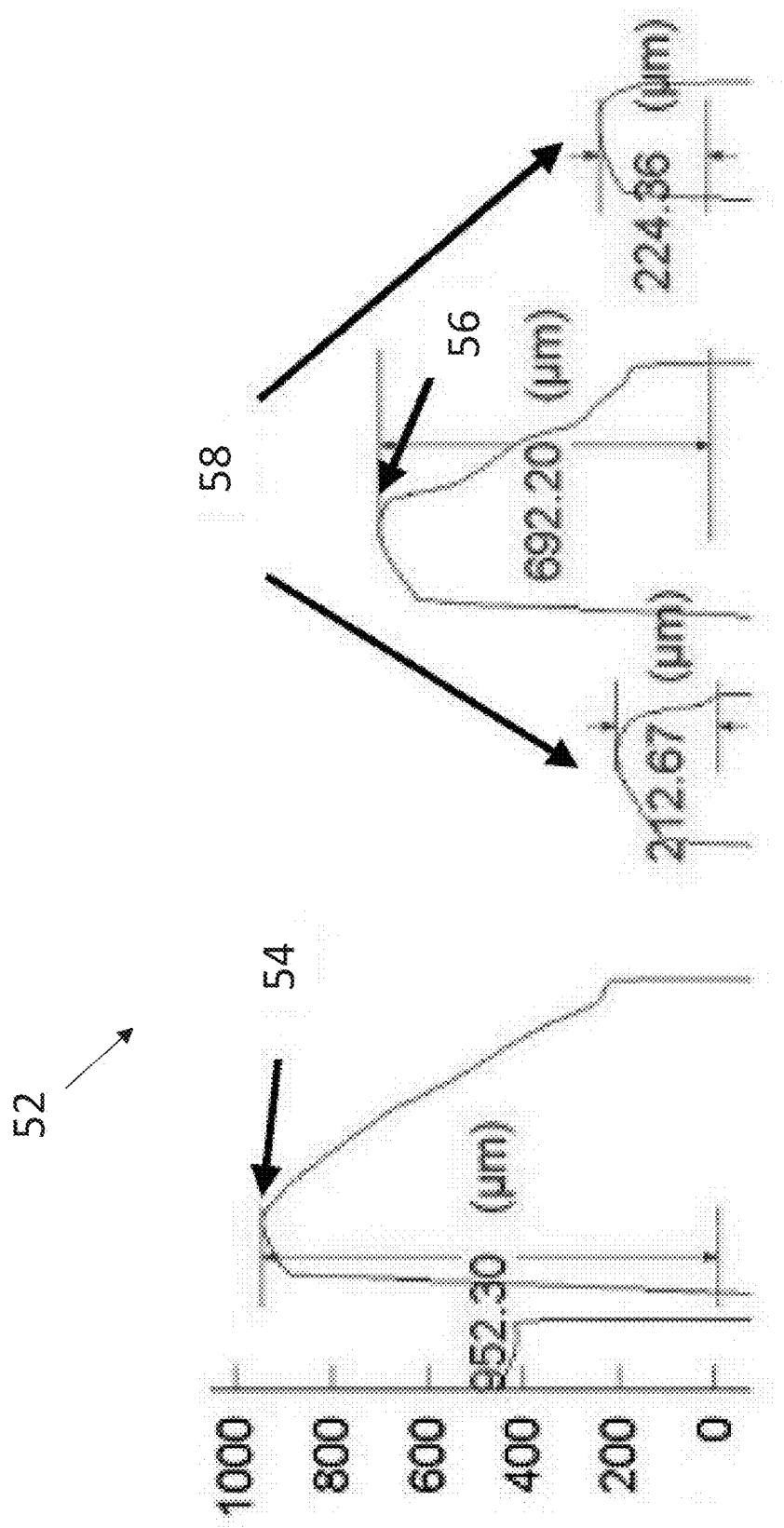
FIG. 8 is a non-limiting profile representative of one embodiment of an acquisition distribution layer according to the present invention.

FIG. 8 is a Z direction profile 52 of the multi-tier, tri-planar film 44 shown in FIG. 7 (a similar profile will also exist for the film 34 shown in FIG. 5). The Z direction profile 52 may be measured by a profilometer, such as a GFM device. Upper tier expanded leather grain artwork lands 54 may be in a higher plane than mid-tier leather grain artwork lands 56, and 40 mesh lands 58 are in the lowest plane for the bottom or lowest tier. The top plane of the top tier lands 54 may extend from the base of the formed film 44, which is also the plane of the apex of the openings or the lowest bottom plane of the formed film sheet 44, with a total loft or Z direction height of about 950 microns. The top plane of the middle tier lands 56 may extend from the base of the formed film with a total loft or Z direction height of about 690 microns. The difference between the top tiers 54 and middle tiers 56 may be, therefore, about 260 microns in this embodiment. The top plane of the lower tier lands 58 may extend from the base of the formed film 44 with a total loft or Z direction height of about 220 microns. The difference between the middle tiers 56 and lower tiers 58 may be, therefore, about 470 microns in this embodiment.

This separation of the heights of the tiers 54, 56, 58 is functional in that the upper tier lands 54 may create a low land surface area to enhance low skin occlusion and low residual wetness. The second tier lands 56, being a bit lower, may still provide the visual effect for camouflage when viewed from above when the parent looks down on the diaper. Since the lowest tier lands 58 have the greatest separation of height, they may not be seen by the eye, and they also may create the buckets or wells for fluid acquisition into the film to be either distributed or absorbed. The height differences between the top planes of each tier 54, 56, 58 of a multi-tier formed film 44 may vary as desired, provided the above described rule that the screen's thickness exceeds the resulting film's thickness.

Figure 9:
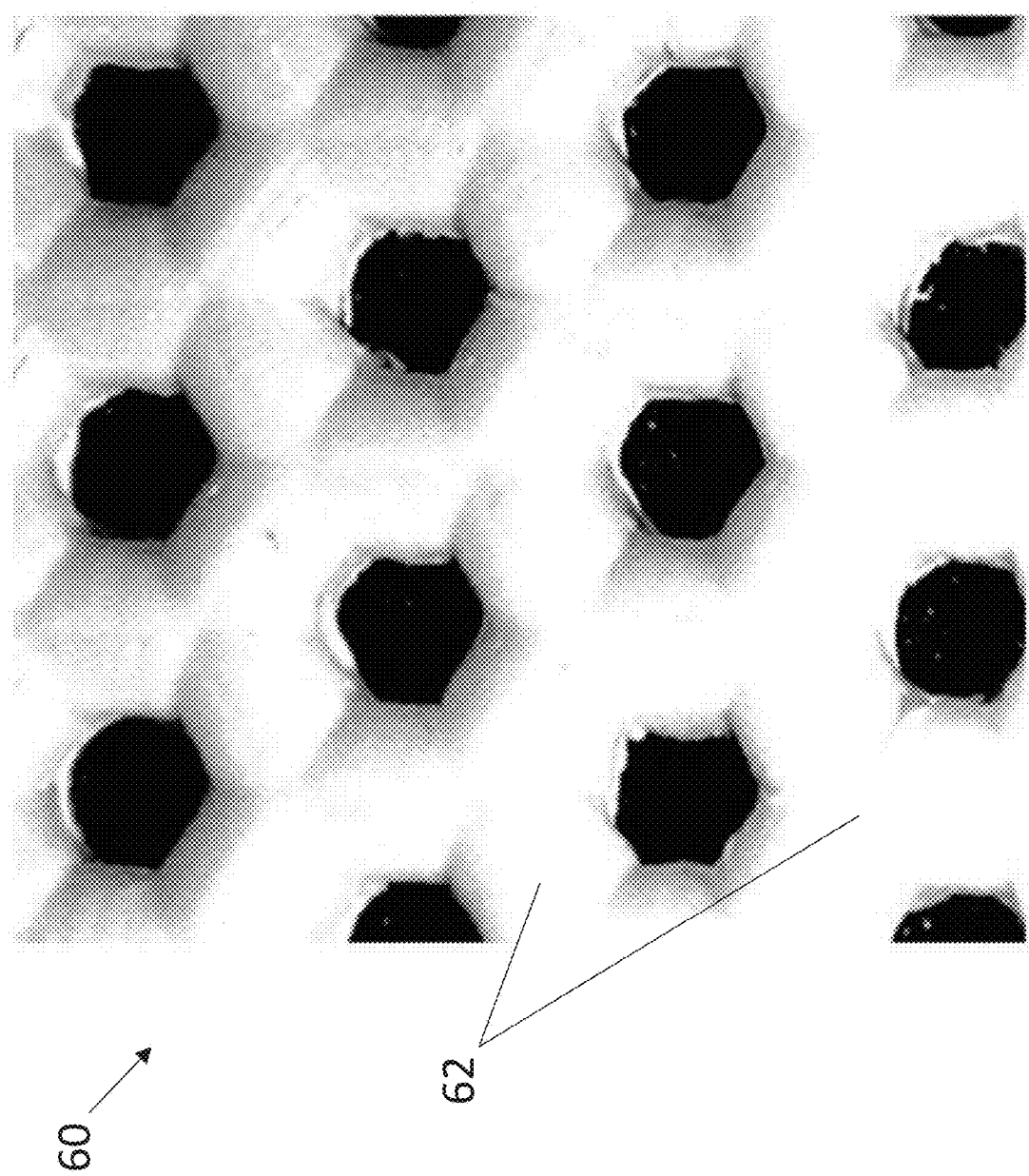
FIG. 9 illustrates an acquisition distribution layer with a repetitive pattern of hexagonal cells.

In an example, the top plane of the leather grain artwork lands (upper tier lands 54) is greater in height from the next middle tier's top plane (middle tier lands 56) such that the pressure of a baby's buttock pressing against the topsheet of a diaper will not allow the skin to penetrate to a depth that can reach the plane of the second tier (the middle tier lands 56). In this way the top plane land surface area can concurrently determine the percent of skin occlusion area and residual wetness area. Referring to FIG. 9, which illustrates a current acquisition distribution layer with a repetitive pattern of cells of the geometric shape of a hexagon. The mesh count of this acquisition distribution layer film 60 may be 11.2 mesh and may be similar to acquisition distribution layer materials described by U.S. Pat. No. 6,610,904 and European Patent No. EP 1 318 781 B2.

Figure 10:
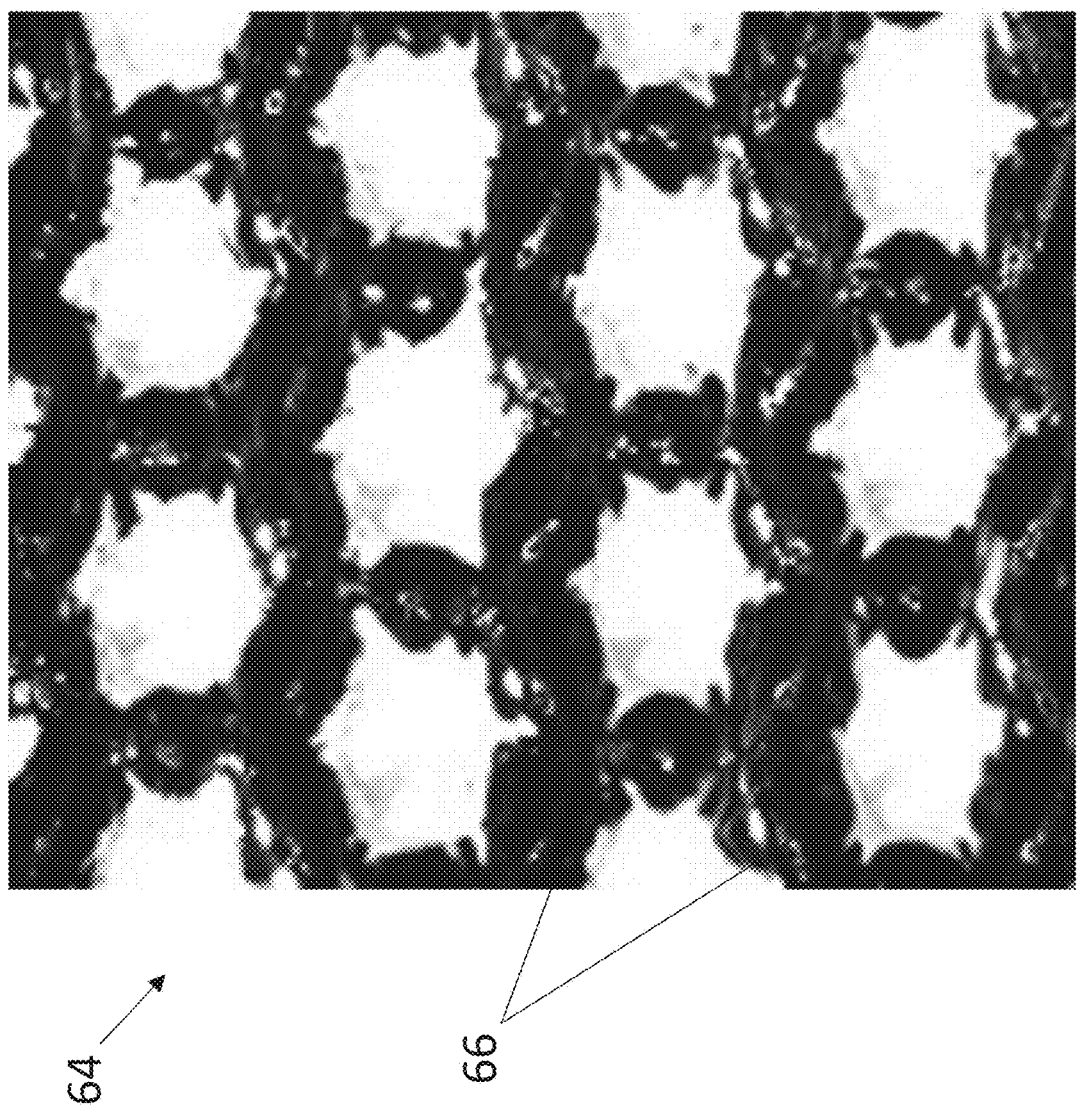
FIG. 10 is an example of an inked film, after the film illustrated in FIG. 9 has been treated with black ink.

FIG. 10 depicts the same film 60 illustrated in FIG. 9, only in inked form 64. In this illustration, the lands 62 were treated with black ink, in order to determine the percent value of land surface area. To apply black ink to the lands 62, a hard polymer roller may be run on an ink pad of black ink until its surface may be well or sufficiently coated with black ink. The roller may then be gently rolled on the acquisition distribution layer's top surface, generally called the "female side" in the current examples for apertured formed films used in absorptive devices, until the land surface area 62 is coated in black ink. The inked film 64 may then be put under the ImagePro unit and a program for determining the value for "area" may be selected. The ImagePro unit can see the contrast between white and black and the technician selects the computer option to "see" the black area 66. The black area 66 may then be calculated as a percent of the total area in the segment area seen in total by the ImagePro unit at a given magnification. FIG. 10 provides one example of what the ImagePro unit "sees." Lower magnifications may be generally selected in order to see more film area to get a better assessment of the contrasting areas. In practice, several sample areas of the inked film 64 are tested to determine the average value and the standard deviation of the data, if desired. Using this methodology, the land surface area shown in FIG. 10 (i.e., the area of the inked film 64) for the 11.2 hex acquisition distribution layer film 60 of FIG. 9 is found to be 57.5%. In this example, the area of the inked film 64 represents the area of wetness and skin occlusion realized by the user. While an area of 57.5% may be functional and consistent with materials that can be purchased today and that are used in many diaper brands currently, an area of 57.6% may not be considered to be ideal.

Figure 11:
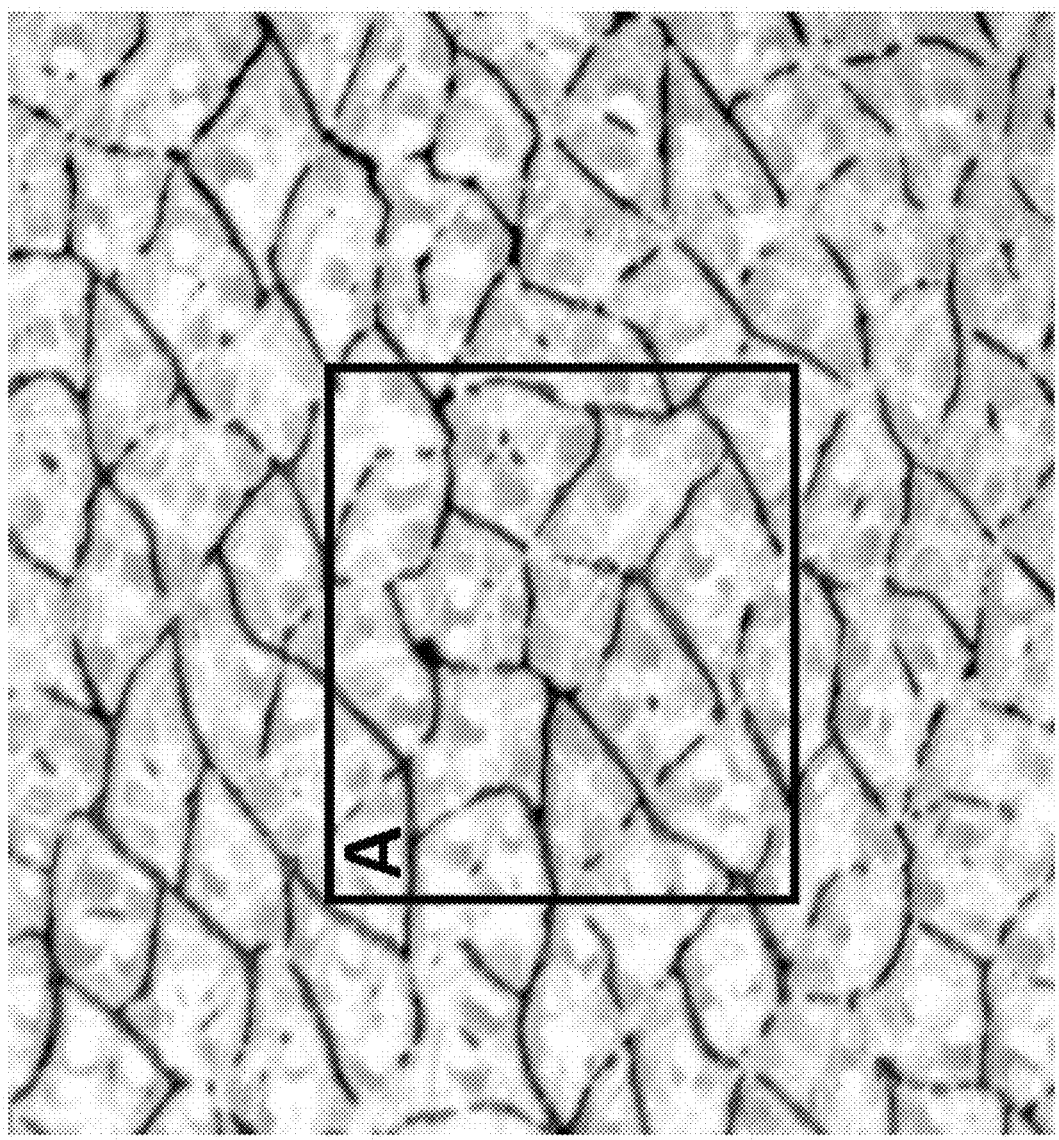
FIG. 11 is an example of an inked film having the irregular cell pattern consistent with one or more embodiments of the acquisition distribution layer of the present invention.

The difference in land surface area of the examples herein may be shown in FIG. 11, which, as discussed above, is a graphic showing black ink applied to the upper-most tier's land surface area (such as upper tier lands 54 identified in FIG. 8), which may be in direct contact with a topsheet 12, which is then in direct contact with user's skin. The percent of land surface area of this film 68 is constructed to be consistent with the preferred film 34 of FIG. 5. The film 68 is contemplated to include two upper tiers (encompassing, for example, the upper and middle tier lands 54, 56 identified in FIG. 8) of leather grain artwork, the uppermost tier (encompassing, for example, the upper tier lands 54 identified in FIG. 8) being expanded 70% in scale beyond the scale of the leather grain artwork of the mid-tier (encompassing, for example, the middle tier lands 56 identified in FIG. 8), with the lower tier (encompassing, for example, the lower tier lands 58 identified in FIG. 8) having a repetitive pattern of cells with a land perimeter geometry of a pentagon. The percentage of land surface area of the film 68 is 10.5% to 12.5%, depending on the exact area selected to place within the ImagePro's image area. It is noted that reference to the upper, middle, and lower tiers and associated lands 54, 56, 58, whether here or in other areas of this application and/or drawings, is intended to be generic to several of the embodiments of the present invention. To that end, reference to the tiers and lands with respect to any particular embodiment is not intended to exclude any other embodiment.

Figure 12:
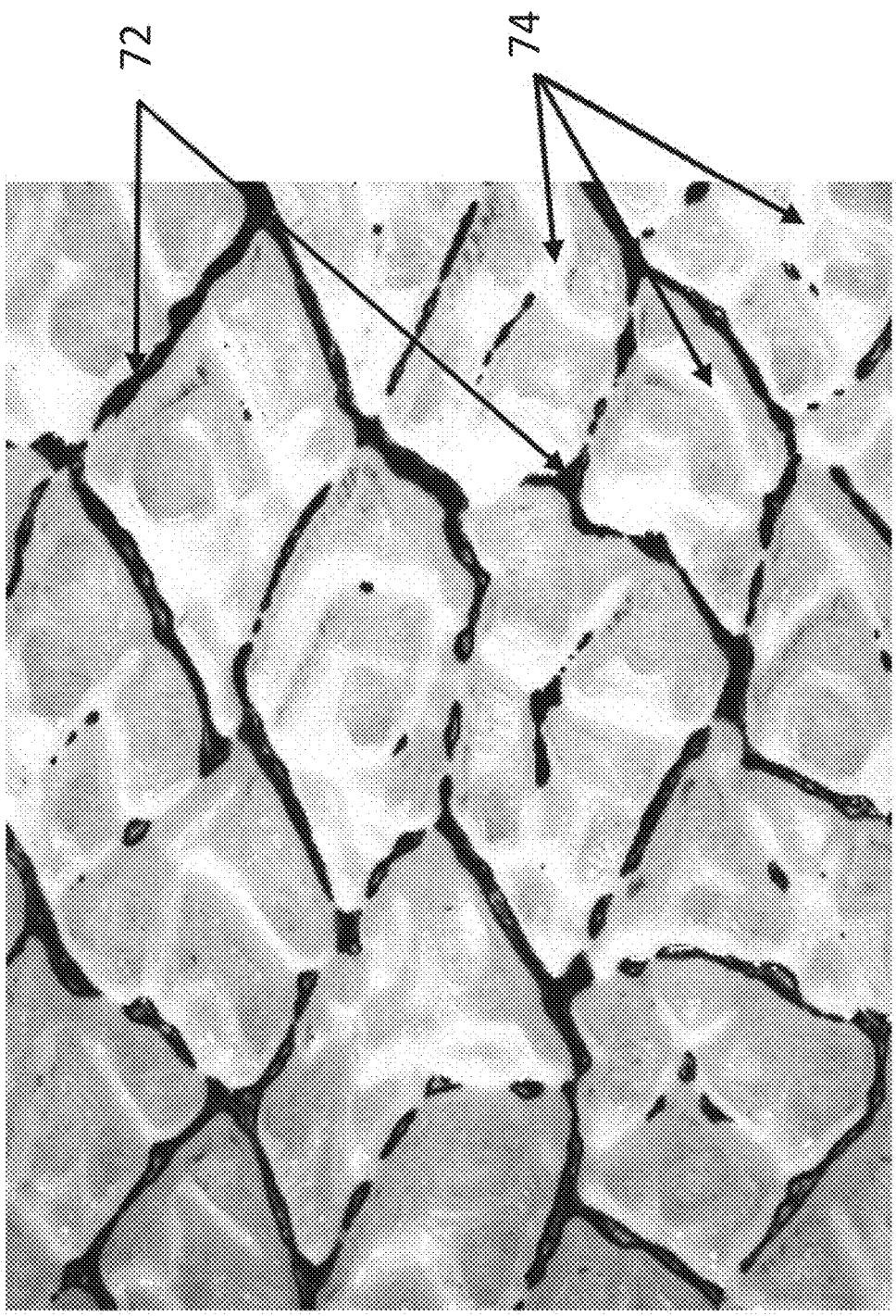
FIG. 12 is an enlarged detail of the inked film provided in FIG. 11.

FIG. 12 shows a film segment 70, which is the enlarged view of segment A of the film 68 shown in FIG. 11. The film 68 encompasses structure consistent with a leather grain artwork. The film segment 70 may have an upper tier land surface area for the upper tier lands 72 that may be in contact with the topsheet 12. The film segment 70 also includes a mid-level tier of lands 74 beneath the upper tier lands 72. The mid-level tier of lands 74 are contemplated to help the acquisition distribution layer to be invisible. The mid-level tier of lands 74 may not be substantially in contact with the topsheet 12.

By variations of land widths and by reliance on the expansion factor utilized in the upper-most tier's leather grain artwork, the percent land surface area of this example can range from 8.5% to at most about 25%. Land surface areas above 25% may begin to lose the good functionality achieved by lower land surface area percentages. Typically, when at least two tiers of leather grain artwork (i.e., upper tier lands 72 and mid-level tier lands 74) may be applied, the land surface area percentage may range, region to region, from about 10.5% to about 12.5%. The land surface area may become the residual wetness area when the nonwoven topsheet 12 is employed. As noted, the residual wetness area is where moisture can become trapped at the interface between the nonwoven topsheet 12 and top plane of the film's lands. The residual wetness area also may be the skin occlusion area. As noted, the present invention provides for an acquisition distribution layer 18 that reduces the residual wetness area and greatly helps to improve skin health and comfort.

As discussed above, by providing a leather grain artwork on at least the upper tier lands, the acquisition distribution layer 18 may become "invisible" to the naked eye when viewed in a diaper with a nonwoven topsheet 12. Table I below shows that a panel of ten parents, who are recently familiar with the use of baby diapers, were overwhelmingly unable to discern the negative appearance of the prior art's repetitive pattern of geometrically shaped depressions when the leather grain artwork was utilized.

Diaper-like pads were prepared with the 11.2 hex acquisition distribution layer of prior art in Pad "A" and the preferred embodiment leather grain artwork acquisition distribution layer 34 of FIG. 5 of this art in Pad "B." The Pad "B" acquisition distribution layer 34 had two tiers of leather grain artwork and bottom tier of 17.5 mesh repetitive pentagons. The panelists were asked to observe the pads by sight and touch and answer the question: "Can you discern a repetitive pattern of depression in Pad A or B? Answer with a, 'Yes,' 'No,' or 'Not Sure'." Panelists were selected from males and females of various ethnicities. The panelists also were selected from a broad age group.

It may be noted below that 8 out of 10 parents were unable to "see" the negative appearance of a repetitive pattern of depressions. Two (2) of the parents were unsure. Thus, the leather grain artwork acquisition distribution layer can be deemed as "invisible" and does not signal to a parent the potential for skin marking, as experienced with prior art materials. As noted, the prior art produced skin markings that parents interpreted as a rash.

The results of the panel test are tabulated in Table I, provided below.

TABLE I

Results from Panel Test

| Panelist | Pad "A" | Pad "B" |
| --- | --- | --- |
| 1 | Yes | No |
| 2 | Yes | No |
| 3 | Yes | No |
| 4 | Yes | No |
| 5 | Yes | Not Sure |
| 6 | Yes | No |
| 7 | Yes | No |
| 8 | Yes | No |
| 9 | Yes | Not Sure |
| 10 | Yes | No |

The forming screens used to produce the acquisition distribution layer 18 of the present invention will now be discussed.

Figure 13:
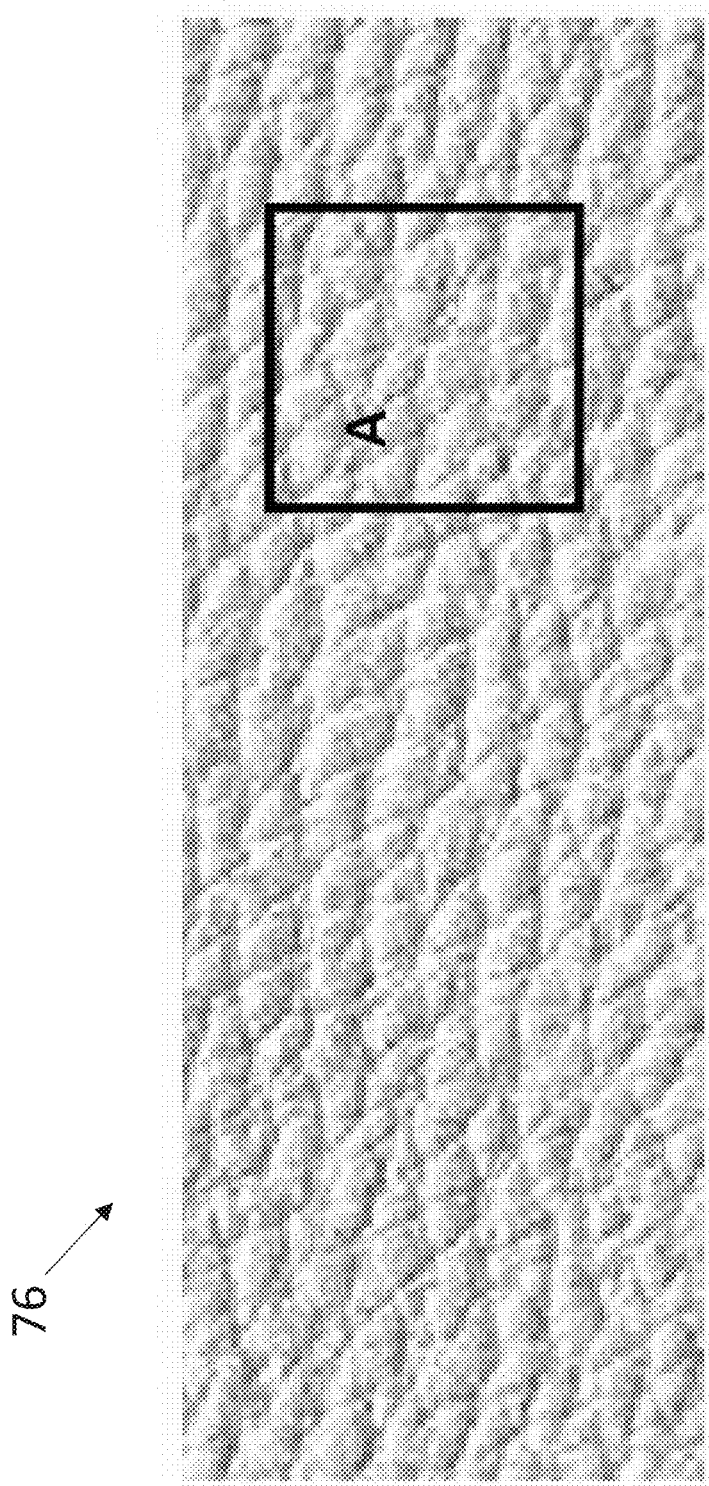
FIG. 13 is an illustration of an embossed vinyl sheet of the type often used in the automotive industry as synthetic leather.

FIG. 13 is a picture of an embossed vinyl sheet 76 of the type often used in the automotive industry as "synthetic" leather. The leather grain artwork embossed into the vinyl sheet 76 is often used as dash board cover or seat upholstery and the like. To obtain synthetic leather, the vinyl sheet 76, or other suitable material, may be embossed with the leather grain artwork. Embossing may typically be done in a pressurized nip where a hard roll has the artwork's features in it and it is pressed into a corresponding rubber roll where the softer rubber compresses in the artwork's raised array on the harder embossing roller. The vinyl sheet 76 may be fed into this nip and at the right temperature and pressure the leather grain artwork is transferred from the hard roller into the vinyl sheet 76.

The hard rollers may be (e.g., are often) comprised of an outer layer of hard ebonite, or one of a variety of types of synthetic thermoset rubber materials, that is then laser engraved with the leather grain artwork. Laser engraving may be particularly suitable for artwork that lacks regular, repetitive patterns, which can readily be engraved into embossing rollers by mechanical means similar to knurling. In laser engraving, however, virtually any artwork the eye can see can be replicated into laser "artwork" which commands the laser's on and off cycles, and the power applied during the "on" cycle moments, to remove or leave material, thus replicating the artwork seen by the eye. Coincidentally, as well, in an example (e.g., as described in U.S. Pat. No. 8,460,778 (the content of which is incorporated herein by reference)), laser engraving a layer of thermoset rubber with fine scale elements that may survive the direct melt vacuum forming process, the process most commonly used for making formed film acquisition distribution layer materials, may be used. In one or more embodiments, and especially the preferred embodiment of the leather grain artworks utilized for examples herein, a material may have regions where fine scale lands of close proximity lay upon lower tier lands may make such a screen making methodology important for those examples.

Figure 14:
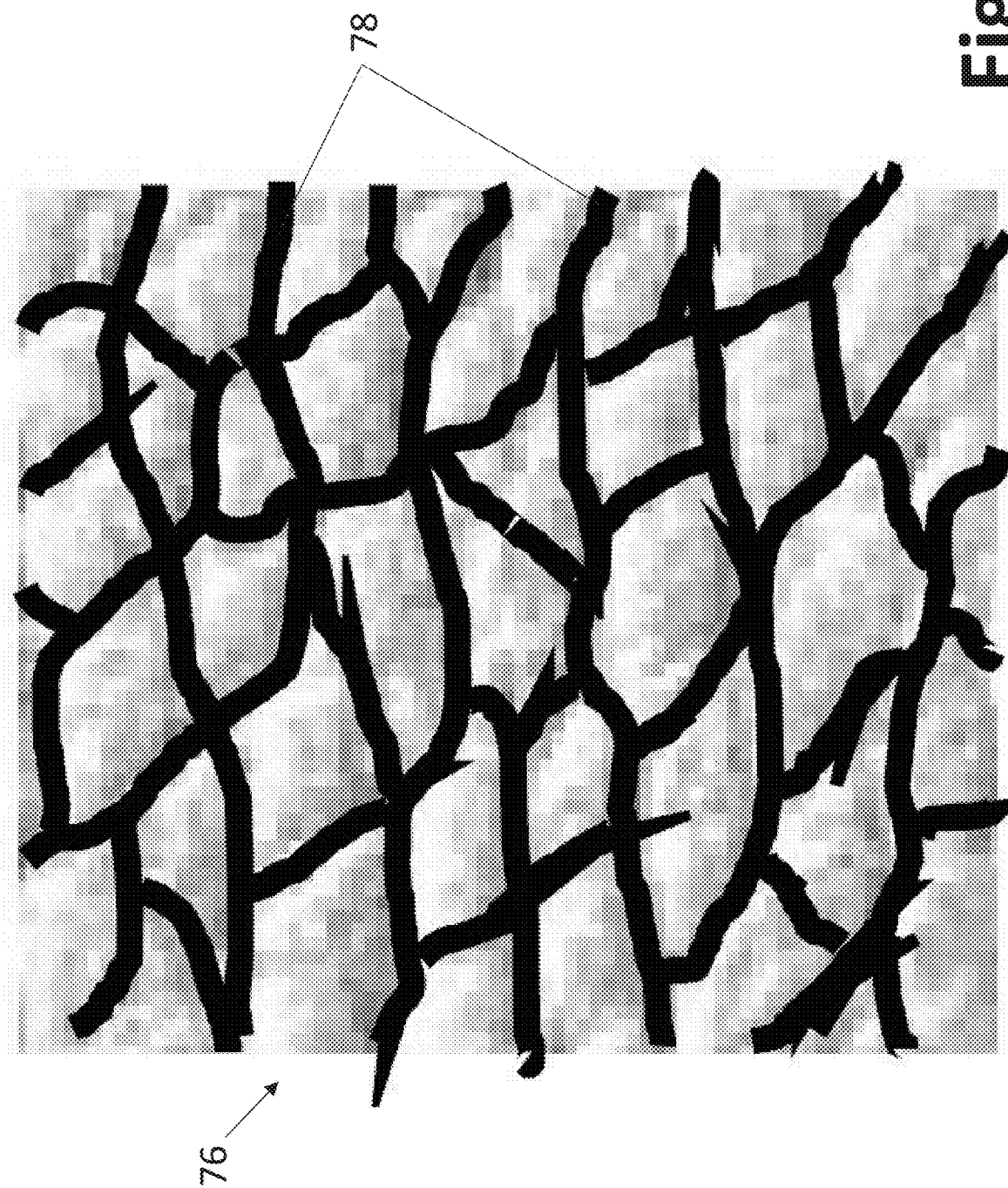
FIG. 14 is an enlarged detail of the embossed vinyl sheet illustrated in FIG. 13, where lines have been traced over the valleys of the depressions in the grain of the synthetic leather illustrated in FIG. 13.
Figure 15:
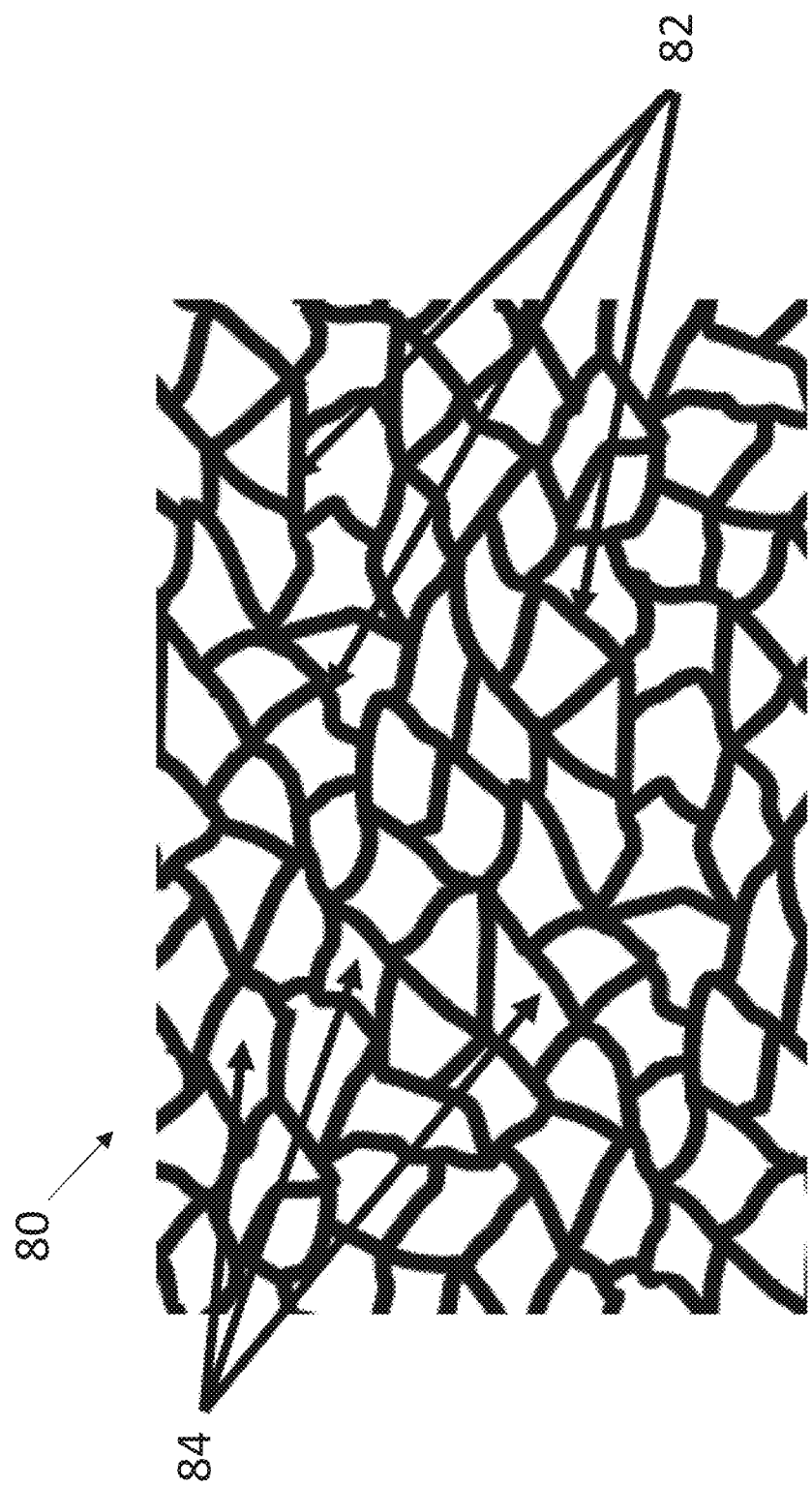
FIG. 15 is a graphical illustration of an example of an artwork created from the lines traced in FIG. 14, where the artwork may be used for guiding a laser to create a template for manufacturing an acquisition distribution layer according to the present invention.

To impart a leather grain artwork to a formed film acquisition distribution layer 18, the following may be employed. Referring to FIG. 14, which is an expanded view of the section A of the vinyl sheet 76 shown in FIG. 13, lines 78 may be traced over the valleys of the depressions in the leather's grain. In FIG. 15, the lines 78 may be then used to create the artwork 80 for guiding the laser. The lines 78 may be used to establish the perimeters 82 of the forming cells 84, thereby outlining the shapes of cells 84. The artwork 80 also may be drawn to a pre-described width so the laser may cut a narrow land width in the forming screen.

The leather grain artwork can be expanded or reduced to change the scale of the artwork 80, as desired. In embodiments shown herein, for example, the leather grain artwork 80 may be expanded and placed over the original scale of the artwork 80. This artwork 80 may guide the laser to engrave a multi-tier effect where the expanded grain is in a first top tier and the original grain is in a second lower tier. When this type of forming screen is used to make apertured formed film 18, the film 18 may have multiple tiers, as explained in greater detail above.

Figure 16:
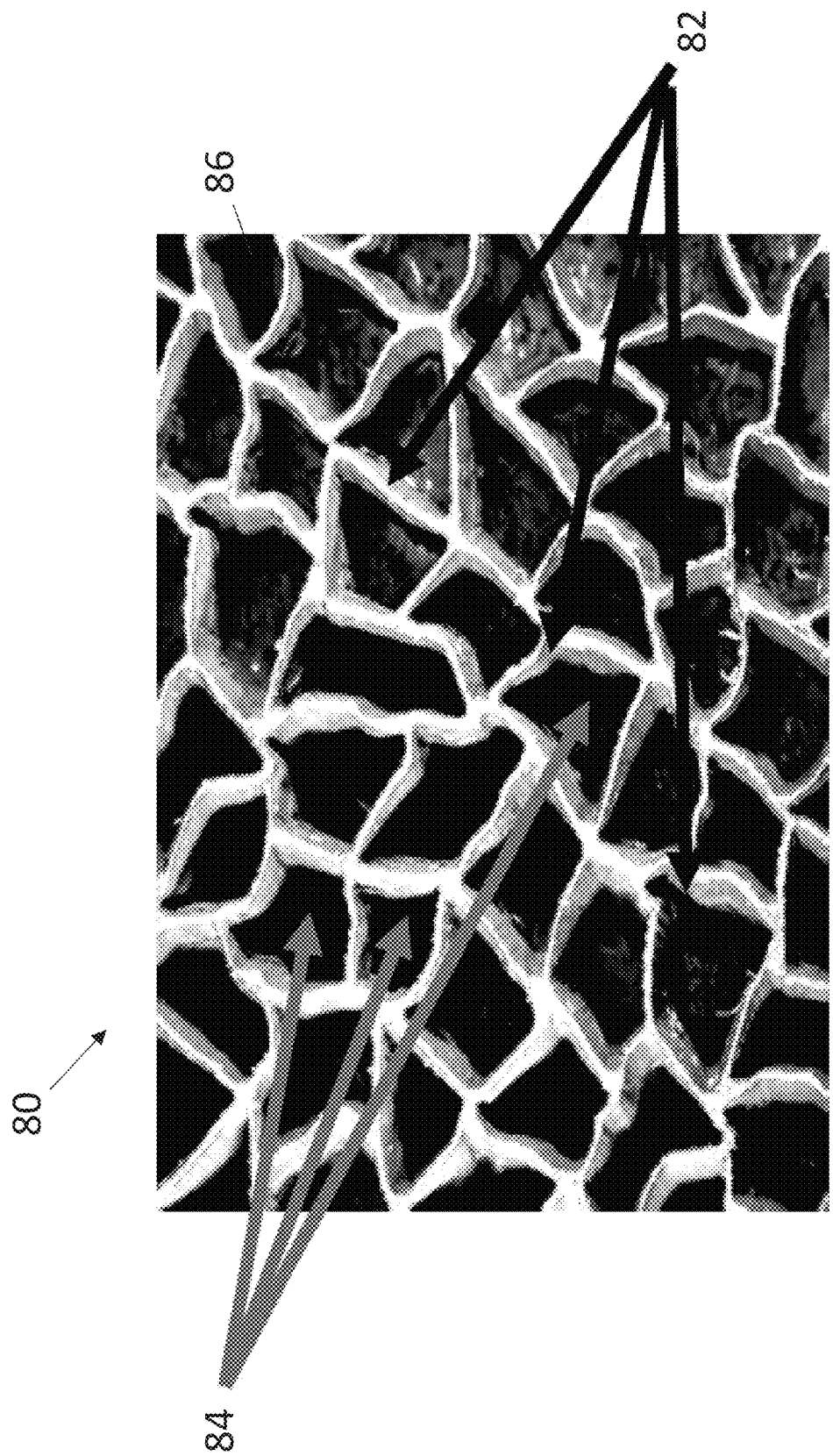
FIG. 16 is an illustration of a single tier of leather grain artwork engraved into a thermoset rubber layer.

Referring to FIG. 16, a picture of a single tier of leather grain artwork 80 engraved into a thermoset rubber layer 86 is shown. Forming cells 84 are surrounded in their perimeter by lands 82. The forming cells 84 and lands 82 may have a common depth, forming a single tier thickness of 1650 microns. In the example scale used in FIG. 16, an inscribed circle placed within a cell's land perimeter 82 may range in diameter from about 800 microns to 1400 microns. This may help the vacuum forming process to essentially open each of the cells in the film. If larger holes than this exist in close proximity to smaller holes than this, once the larger holes opened, the air flow required to open the holes may reduce the vacuum pressure leaving insufficient force to open the smaller holes. Without sufficient formed film open area where some smaller cells remain unopened, the fluid acquisition rate may decrease and fluid lying in the unopened cell buckets could increase residual wetness.

The depth or loft of the single tier formed film 20 is created when the forming screen 32 of FIG. 4 is used in a vacuum formed film process may be (e.g., essentially) determined by the largest size of the inscribed circle within a cell 28. Since the largest cells 28 herein may be about 1400 microns, it becomes possible to produce a formed film 20 with a loft of almost about 1400 microns. Since the forming screen 32 of FIG. 4 has a tier thickness of 1650 microns, it may be thicker than the resulting formed film's loft of about 1400 microns. This may be important to the vacuum formed film process since the forming screen 32 runs across a stationary vacuum slot. If the film 20 formed cells of a loft that reached deeper through the screen 32 than the thickness of the screen 32, the formed cells 24 may be distorted by dragging across the seal. In multi-tier embodiments (e.g., described herein below), this factor may be determined by the opening size of the lowest tier cells whose bottom plane may be in direct contact with a vacuum seal.

The segment of the forming screen 32 having the leather grain artwork 80 may be formed by acid etching through a sheet of 316 Stainless Steel (SS) that may be 255 microns thick. The leather grain artwork 80 may be applied to the surface of the SS sheet in the form of an acid resist material layer such that the acid can only etch through the SS where the openings of the forming cells 28 are to exist. Where acid etching is resisted, the land array 30 remains. Six identical sheets may then be stacked in alignment vertically and bonded together yielding the forming screen 32 with the leather grain artwork 80 that is 1530 microns thick (6×255 microns=1530 microns). The thickness of the forming screen 32, as explained herein, may be greater in thickness than the 1400 microns of the resulting film 20, which protects the cell shape integrity on the lowermost plane of this single tier formed film 20. Again, in the acid etched screen 32 shown in FIG. 4, the forming cells 28 may be surrounded in their perimeter by lands 30. The artwork 80 for the acid resist layer may be again designed to yield a narrow land width.

Figure 17:
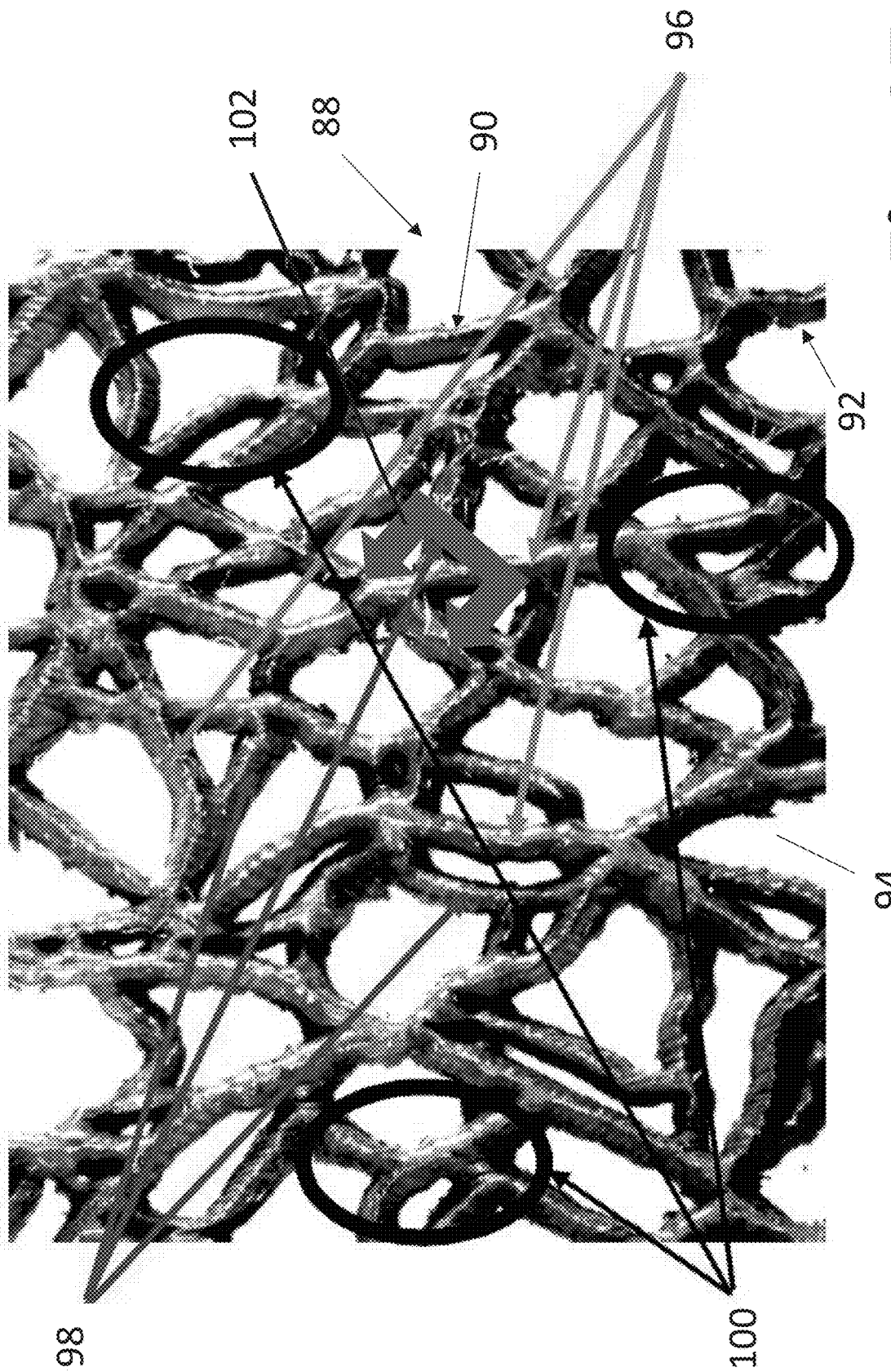
FIG. 17 illustrates an example of a thermoset rubber forming screen according to the present invention.

FIG. 17 provides a picture of a segment of a thermoset rubber laser engraved forming screen 88 with two tiers 90, 92 of the leather grain artwork 80. For the uppermost tier 90, the leather grain artwork 80 may have been expanded to be about 70% larger in scale than the leather grain artwork 80 of the second, lower tier 92. The upper tier lands 96, also called herein the land perimeter of a cell 94, exist in a higher plane. The lower tier lands 98 exist in a lower plane. Also noted by ellipses 100, in a few of the selected random spots where this phenomenon exists, there may be fine scale structures of narrow lands that are spaced apart at a distance of less than 255 micron and are formed on at least one surface of the thermoset rubber lands of the lower tier lands 98. Being a thermoset rubber, however, these exposed fine scale structures may not be at risk for melting in the direct melt formed film process, which may be commonly used for making apertured formed film acquisition distribution layer materials.

Figure 18:
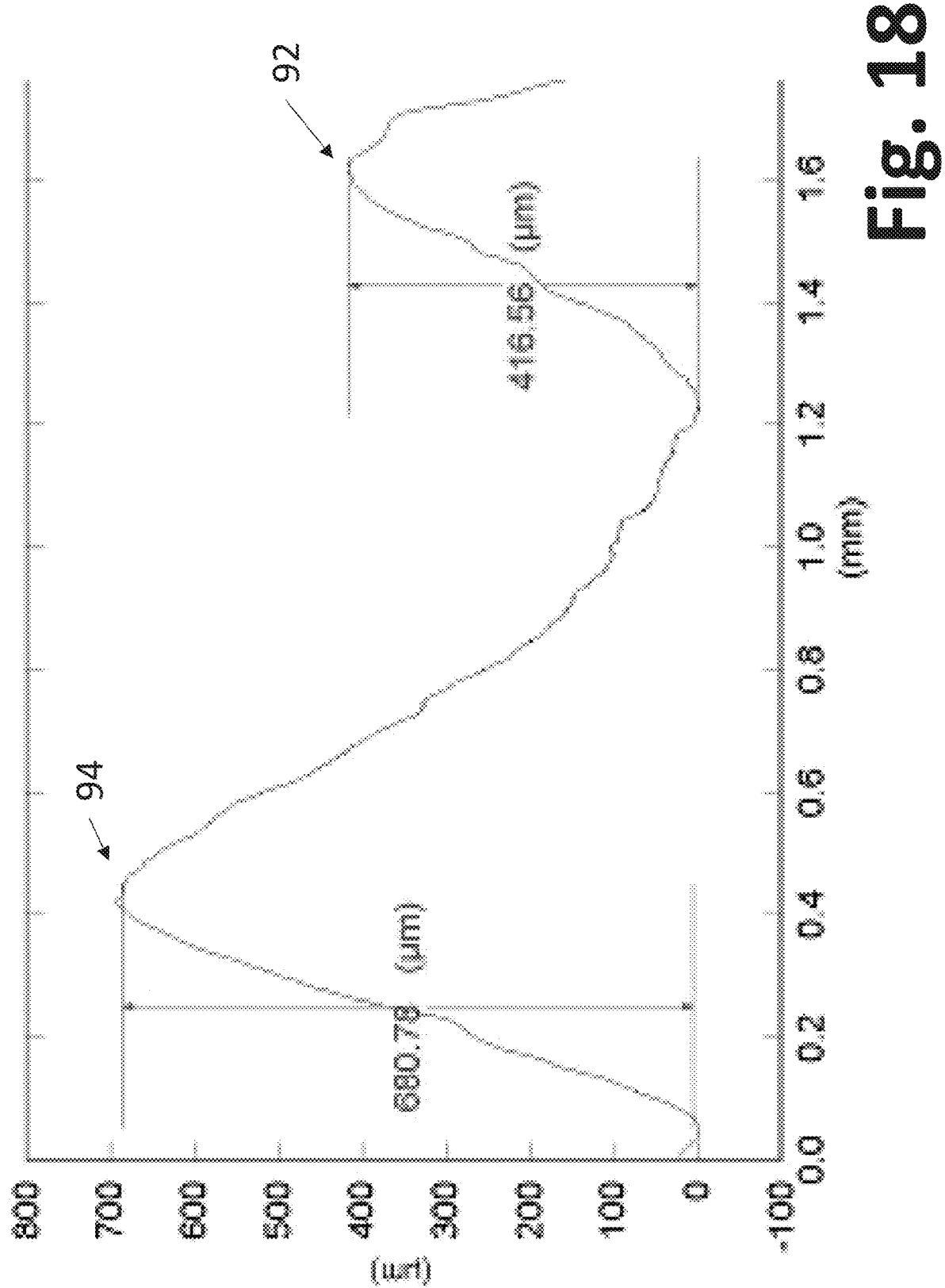
FIG. 18 shows a Z direction profile line, drawn across upper and lower tier lands along the arrows indicated in FIG. 17.

FIG. 18 shows a Z direction profile line, drawn across upper and lower tier lands along the arrows 102 indicated in FIG. 17, where the upper tier height in the Z direction may be greater than the lower tier height in the Z direction. This profile measurement may be accomplished on the GFM device. Height differences may vary from about 100 microns to 500 microns. As shown in FIG. 18, the height of the lower tier 92 is about 420 microns, with the upper tier 94 height being about 680 microns, yielding a tier height difference of about 260 microns. This construction may be suited for the expected performance criteria of the examples herein.

The leather grain artwork screens formed by etching metal and stacking their layers is suitably robust, but etching has limitations of hole size variation and thus some leather grain artworks 80 may not be amenable to the etching method. Thus, the laser engraving of thermoset rubber may be desired or preferred, just as it may be desired or preferred because it may not have such a limitation regarding the range of inscribed circle diameters, as described above.

According to an example, a thermoset rubber forming screen, even if hardened to a 90 Shore D hardness, may lack robustness on its own to survive the stresses of the vacuum formed film process. Making the rubber any harder can also stiffen the rubber and there is some need for ductility in a forming screen. Accumulative micro-stresses of the formed film processes can cause the forming screen to crack if it lacks ductility. Therefore, a base layer underneath the rubber engraved layer adds strength to the rubber engraved layer. An exemplary method is described in U.S. Pat. No. 8,460,778, which is incorporated herein by reference. This base layer which provides for torsional and flexural robustness must also have openings or porosity such that the vacuum suction of the formed film process is transmitted to the upper forming portions of the screen. If positive pressure is applied, like high pressure water nozzles, for example, the porosity of the base screen may be used in order to evacuate the buildup of water which reduces the impact force of the high pressure water droplets by absorbing the force.

If one does not want the base support layer and its pattern of perforations (for transmitting suction) to become a part of the final multi-tier pattern, then the rubber tier of the leather grain artwork 80 may be thicker than the largest opening, similar to requirement above that avoids cell distortion from abrasion from contacting the vacuum seal's surface. In this manner the largest cells in the formed film may not form to a depth greater than the Z direction depth of the rubber engraved tier(s) of leather grain artwork 80, and thus the base support layer, or "base screen," may not be involved in the formation of the formed film cell.

If, on the other hand, it is intended that the base screen's cells may form the lowermost tier 92 of a multi-tiered formed film, then conversely the depth of the upper tier 90 or tiers needs to be thinner than the largest cell of the tier immediately above the support top plane of the support screen. The thickness of the support screen, may then be thicker than the cell diameter that it will form, so, as described above for a single tier screen 32, those cells may not come into contact with vacuum seal and become distorted. In this manner the films of FIGS. 5 and 7 are made.

Referring to FIG. 6, the preferred embodiment of a forming screen 36 is shown. The upper tier lands 104 in the upper-most top tier 106 and second tier lands 108 are in a second, or middle, tier 110 are seen in the graphic. Lands 104, 108 are comprised of the thermoset rubber laser engraved material. Bottom tier lands 112 are the lands of the base screen. In an example triple-tier forming screen, the base screen may be comprised of metal.

Figure 19:
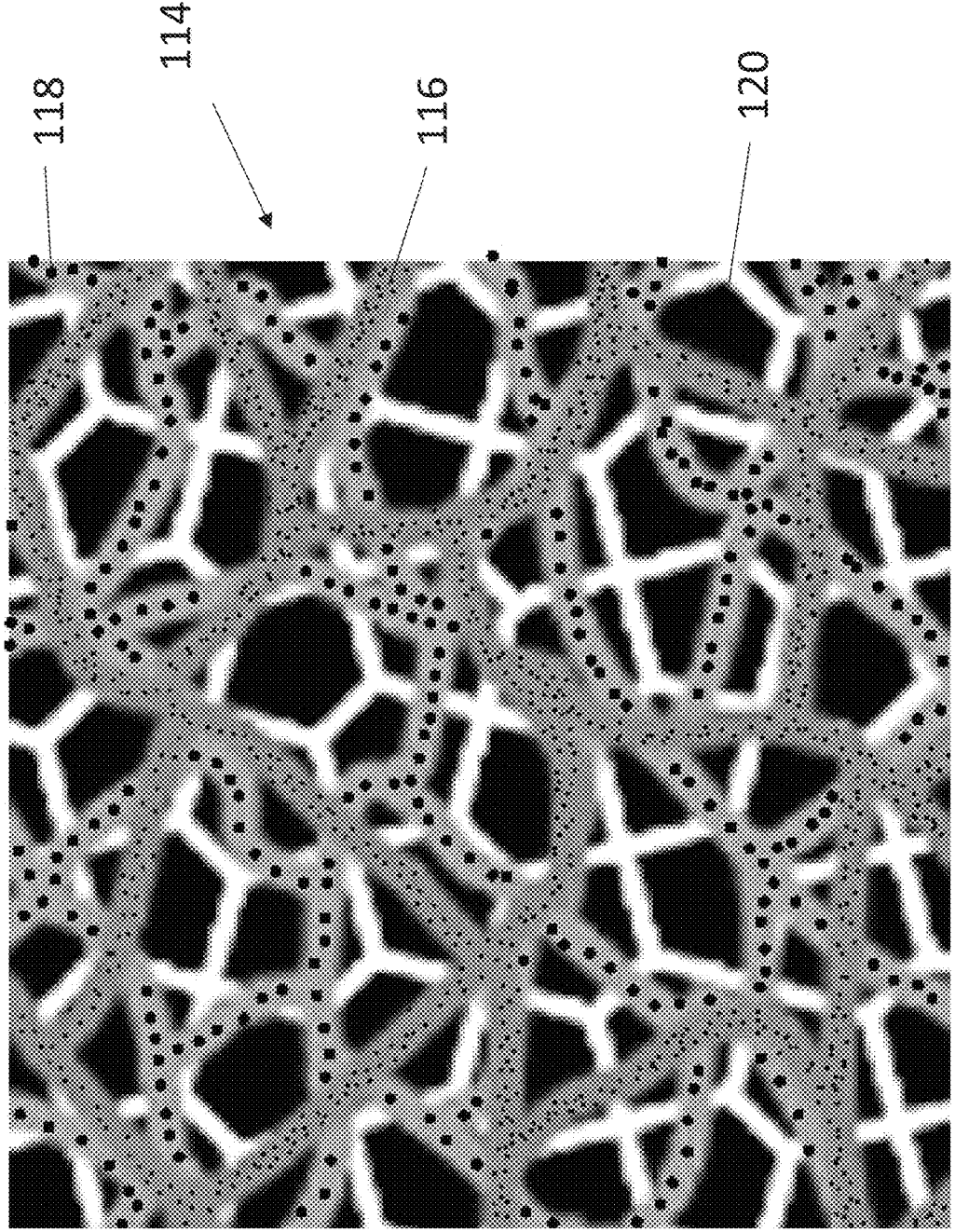
FIG. 19 is a graphic illustration showing three tiers of lands.

FIG. 19 is a graphic illustration where upper tier lands 116 of the expanded scale leather grain artwork 114 are designated with a pattern of smaller dots therein, mid-tier leather grain lands 118 are designated with a patter of larger dots therein, and the lower tier base screen's repetitive pattern of pentagon geometrically shaped cells, i.e., the lower tier lands 120, are drawn without a pattern therein. In the example shown, the pattern of smaller and larger dots are used to designate the tiers and are not intended to represent holes or apertures therein.

Figure 20:
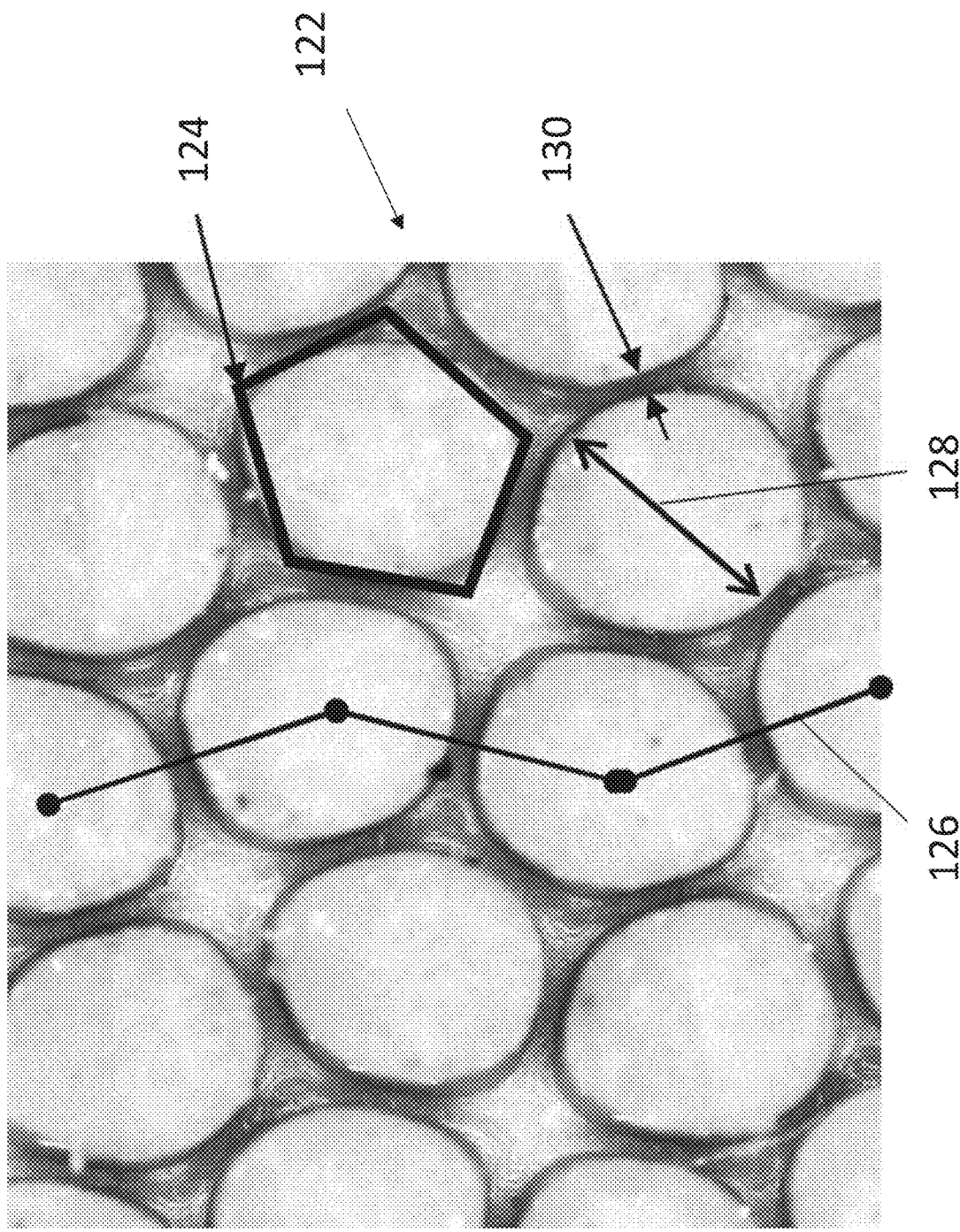
FIG. 20 is a graphic of a base screen according to the present invention.

Referring to FIG. 20, a graphic of a base screen 122 is shown. A segment of the base screen 122 shows a repetitive pattern of pentagons 124. Some metal screen fabrication methods may cause some rounding of the polygon at its corners, as is the case with this particular nickel plated screen shown in FIG. 20. While nesting a pentagon to have narrow lands does not form an exactly straight line of alignment, they may be generally aligned along line 126 and, therefore, one can calculate a "mesh count." For the base screen having the bottom tier lands 112 used in FIG. 6, its mesh count may be 17.5 cells per linear inch. The cells shaped from the geometric polygon of a pentagon 124 may have a diameter 128 of about 1270 microns. The land width 130 may range from 100 to 180 microns.

Figure 21:
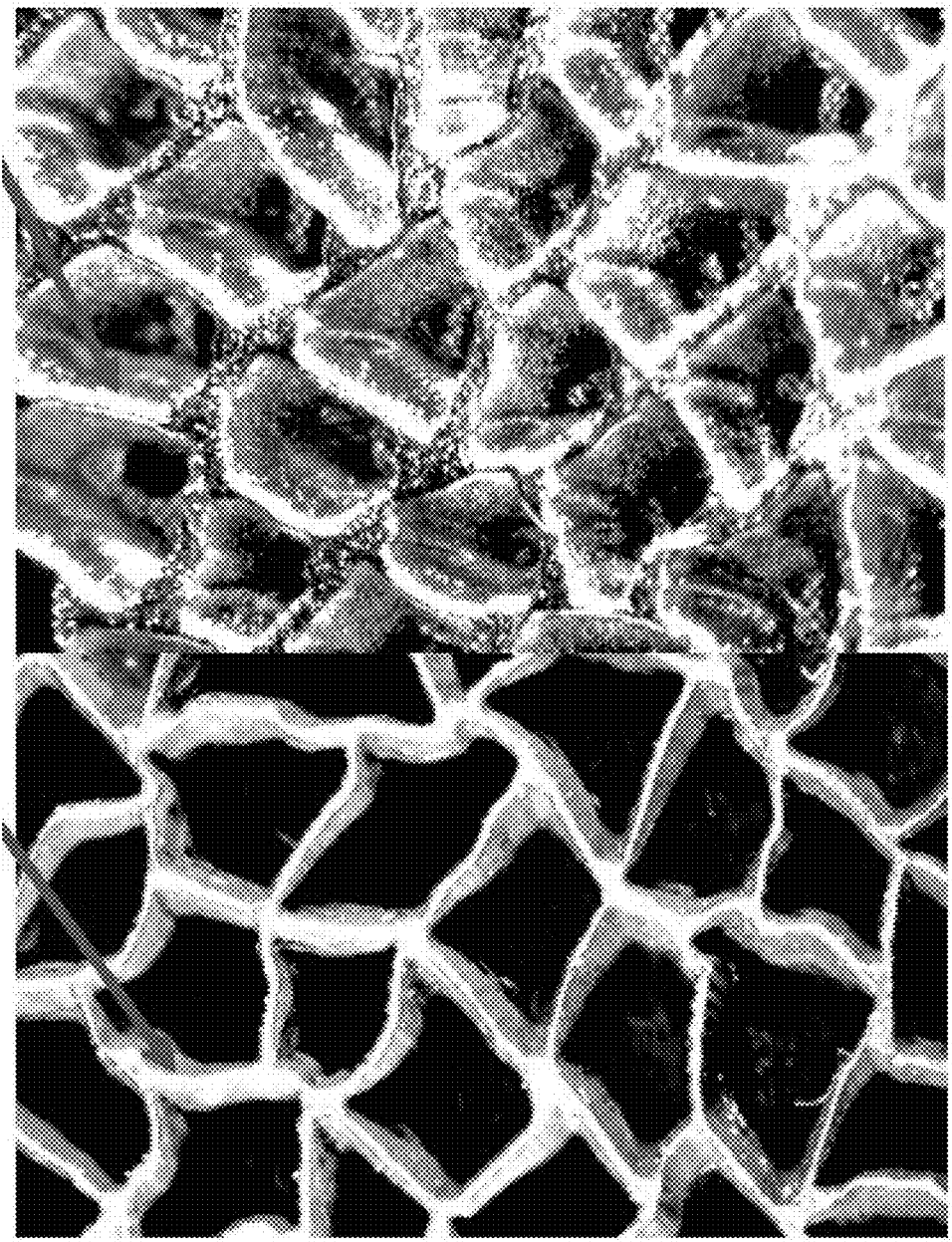
FIG. 21 is a side-by-side comparison of a segment of a thermoset rubber laser engraved single tier forming screen.

FIG. 21 provides a side-by-side picture of a segment of a thermoset rubber laser engraved single tier forming screen 132. Lands 134 on the left show the virgin rubber lands after laser engraving. This screen 132 may run sufficiently without risk of melting on exposed fine scale structure regions, but the lack of heat transfer of rubber may cause it to run at a slower rate. Lands 136 on the right show lands with a Nickel flashing applied. Nickel may add some measure of heat transfer to allow this screen to run a higher rate. The nickel may also aid in the film releasing from the screen after the forming of the film is completed. Nickel flashing is typically done in electroless nickel plating processes. The thickness of the nickel flashing may vary from 5 to 30 microns. Typically a sufficient flashing may have 7.5 to 10.5 microns of nickel thickness, varying slightly from region to region on the screen, due to the irregular aspects of the leather grain artwork.

FIG. 22 provides a graphical, side view of a multi-tier absorptive device 138 according to the present invention. The absorptive device is similar to the absorptive device 10, except that the acquisition distribution layer 140 encompasses an upper tier 142, a middle tier 144, and a lower tier 146. The construction illustrated for the absorptive device 138 is contemplated to be consistent with the various embodiments described above.

The examples herein may provide forming screens with thermoset rubber laser engraved tiers of leather grain artwork in order to form acquisition distribution layer films for absorptive devices (e.g., that may provide benefits to current acquisition distribution layer formed films). The embodiments described herein, while preferred and useful, are in no way intended as limitations to options this inventive art provides.

To help solve the issues current acquisition layer and/or films provide, examples herein may provide leather grain artwork that may be invisible underneath a nonwoven topsheet and could also provide a lower land surface area. In examples, the leather grain artwork simulated into a formed film and having the irregular array of wandering land configurations, camouflages the formed film when the formed film is placed beneath a nonwoven, since a random fiber nonwoven also has irregular, wandering strands of fibers.

The dimensions and values disclosed herein are not to be understood as being strictly limited to the exact numerical values recited. Unless otherwise specified, each such dimension is intended to mean both the recited value and a functionally equivalent range surrounding that value. For example, a dimension disclosed as "100 microns" is intended to mean "about 100 microns."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. An absorptive device comprising:
   a topsheet;
   a backsheet;
   an absorbent core between the topsheet and the backsheet; and
   an acquisition distribution layer between the topsheet and the absorbent core, the acquisition distribution layer comprising a formed film having a plurality of lands that contact a bottom surface of the topsheet and define a first irregular array of cells,
   wherein the first irregular array of cells is comprised of a random variety of shapes forming no regular geometric shapes,
   wherein the first irregular array of cells is configured to render the plurality of lands invisible to a naked eye when the absorptive device is viewed from above the topsheet, and
   wherein at least some of the first irregular array of cells have an inscribed circle diameter of between about 800 microns and about 1400 microns.

2. The absorptive device according to claim 1, wherein the topsheet is a nonwoven topsheet.

3. The absorptive device according to claim 2, wherein the plurality of lands is invisible by being camouflaged with the nonwoven topsheet.

4. The absorptive device according to claim 1, wherein the acquisition distribution layer has a loft of at least about 775 microns.

5. The absorptive device according to claim 4, wherein the acquisition distribution layer has a loft of about 1400 microns.

6. The absorptive device according to claim 1, wherein top surfaces of the plurality of lands generally lie in a plane and have a combined surface area that provides low skin occlusion and low residual wetness.

7. The absorptive device according to claim 6, wherein the combined surface area is less than about 25% of an overall area of the acquisition distribution layer.

8. The absorptive device according to claim 1, wherein the acquisition distribution layer has multiple tiers, and wherein top surfaces of the plurality of lands define an upper tier.

9. The absorptive device according to claim 8, wherein at least one lower tier relative to the upper tier is comprised of a second irregular array of cells.

10. The absorptive device according to claim 8, wherein a lower tier relative to the upper tier is comprised of a regular pattern of geometrically shaped cells having a repetitive pattern.

11. The absorptive device according to claim 8, wherein the multiple tiers includes the upper tier having a loft of about 950 microns, a middle tier having a loft of about 690 microns, and a lower tier having a loft of about 220 microns.

12. An acquisition distribution layer, comprising:
a plurality of lands; and
a plurality of cells surrounded by the plurality of lands,
wherein the plurality of lands define an array of the plurality of cells, and
wherein each of the plurality of cells in the array of the plurality of cells are irregularly shaped, such that the plurality of cells comprises a random variety of shapes forming no regular geometric shapes,
wherein the plurality of lands comprises a surface area that is <25% of a total area of the acquisition distribution layer, and
wherein at least some of the plurality of cells have an inscribed circle diameter of between about 800 microns and about 1400 microns.

13. The acquisition distribution layer of claim 12, wherein the plurality of lands have a loft of about 1400 microns.

14. The acquisition distribution layer of claim 12, further comprising:
a first tier defining a first plurality of lands;
a first plurality of cells surrounded by the first plurality of lands in the first tier;
a second tier defining a second plurality of lands; and
a second plurality of cells surrounded by the second plurality of lands in the second tier,
wherein the first plurality of lands define a first array of the first plurality of cells,
wherein the second plurality of lands define a second array of the second plurality of cells,
wherein each of the first plurality of cells in the first array are irregularly shaped, and
wherein each of the second plurality of cells in the second array are irregularly shaped.

15. The acquisition distribution layer of claim 14, wherein at least some of the first plurality of cells and some of the second plurality of cells have an inscribed circle diameter of between about 800 microns and about 1400 microns.

16. The acquisition distribution layer of claim 14, wherein the first plurality of lands and the second plurality of lands have a loft of about 1400 microns.

17. The acquisition distribution layer of claim 12, wherein the plurality of lands comprises a surface area that is 8.5% to 25% of a total area of the acquisition distribution layer.

18. The acquisition distribution layer of claim 12, wherein the plurality of lands comprises a surface area that is 10.5% to 12.5% of a total area of the acquisition distribution layer.

* * * * *